United States Patent
Rule et al.

(10) Patent No.: US 9,592,161 B2
(45) Date of Patent: Mar. 14, 2017

(54) METHOD OF MAKING PRESSURE-SENSITIVE ADHESIVE ARTICLE INCLUDING ACTIVE AGENT

(71) Applicant: 3M INNOVATIVE PROPERTIES COMPANY, St. Paul, MN (US)

(72) Inventors: Joseph D. Rule, Cottage Grove, MN (US); Jeffrey H. Tokie, Scandia, MN (US); Kim B. Saulsbury, Lake Elmo, MN (US); Deena M. Conrad-Vlasak, Stillwater, MN (US); Kanta Kumar, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 299 days.

(21) Appl. No.: 14/363,444

(22) PCT Filed: Dec. 10, 2012

(86) PCT No.: PCT/US2012/068757
§ 371 (c)(1),
(2) Date: Jun. 6, 2014

(87) PCT Pub. No.: WO2013/090191
PCT Pub. Date: Jun. 20, 2013

(65) Prior Publication Data
US 2014/0363564 A1    Dec. 11, 2014

Related U.S. Application Data

(60) Provisional application No. 61/569,954, filed on Dec. 13, 2011.

(51) Int. Cl.
*A61F 13/02* (2006.01)
*B05D 5/10* (2006.01)
(Continued)

(52) U.S. Cl.
CPC ........ *A61F 13/0283* (2013.01); *A61F 13/025* (2013.01); *A61F 13/0289* (2013.01);
(Continued)

(58) Field of Classification Search
CPC ..................................................... A61F 13/025
See application file for complete search history.

(56) References Cited

U.S. PATENT DOCUMENTS

RE24,906 E    12/1960  Ulrich
3,389,827 A    6/1968  Abere
(Continued)

FOREIGN PATENT DOCUMENTS

CN    1800289 A    7/2006
DE    102009030581    1/2010
(Continued)

OTHER PUBLICATIONS

International Search Report for PCT International Application No. PCT/US2012/068757, mailed on Sep. 20, 2013, 3 pages.

*Primary Examiner* — Xiao Zhao
(74) *Attorney, Agent, or Firm* — Bradford B. Wright

(57) ABSTRACT

A method includes contact printing an active composition onto a surface of a release substrate to form a printed surface. The active composition spontaneously dewets the surface of the release substrate to form active deposits on the surface of the release substrate. The active composition comprises an active agent dissolved or dispersed in an aqueous liquid vehicle. A pressure-sensitive adhesive layer is disposed on the printed surface.

18 Claims, 4 Drawing Sheets

(51) Int. Cl.
  *C09J 7/02*   (2006.01)
  *A61K 9/70*   (2006.01)
  *A61L 15/26*  (2006.01)
  *A61L 15/44*  (2006.01)
  *C08K 5/00*   (2006.01)

(52) U.S. Cl.
  CPC ............ *A61K 9/7038* (2013.01); *A61L 15/26* (2013.01); *A61L 15/44* (2013.01); *C09J 7/0207* (2013.01); *A61L 2300/20* (2013.01); *A61L 2300/606* (2013.01); *C08K 5/0058* (2013.01); *C08K 2201/013* (2013.01); *C08L 2203/02* (2013.01); *C09J 2201/28* (2013.01); *C09J 2429/00* (2013.01)

(56) References Cited

U.S. PATENT DOCUMENTS

| | | |
|---|---|---|
| 3,645,835 A | 2/1972 | Hodgson |
| 4,112,213 A | 9/1978 | Waldman |
| 4,310,509 A | 1/1982 | Berglund |
| 4,323,557 A | 4/1982 | Rosso |
| 4,472,480 A | 9/1984 | Olson |
| 4,595,001 A | 6/1986 | Potter |
| 4,643,180 A | 2/1987 | Feld |
| 4,643,181 A | 2/1987 | Brown |
| 4,728,323 A | 3/1988 | Matson |
| 4,732,808 A | 3/1988 | Krampe |
| 4,737,410 A | 4/1988 | Kantner |
| 5,032,460 A | 7/1991 | Kantner |
| 5,232,702 A | 8/1993 | Pfister |
| 5,717,005 A | 2/1998 | Richardson |
| 5,766,398 A | 6/1998 | Cahill |
| 5,876,855 A | 3/1999 | Wong |
| 5,958,447 A | 9/1999 | Haralambopoulos |
| 6,352,768 B1 | 3/2002 | Hseih |
| 6,432,602 B1 | 8/2002 | van Beek |
| 6,874,421 B2 | 4/2005 | Kitchin |
| 6,974,609 B2 | 12/2005 | Engle |
| 7,097,853 B1 | 8/2006 | Garbe |
| 7,335,377 B2 | 2/2008 | Stern |
| 2003/0017291 A1 | 1/2003 | Fleming |
| 2003/0054025 A1 | 3/2003 | Cantor |
| 2005/0089539 A1 | 4/2005 | Scholz |
| 2006/0034899 A1 | 2/2006 | Ylitalo |
| 2006/0127626 A1 | 6/2006 | Fleming |
| 2007/0039271 A1 | 2/2007 | Fleming |
| 2008/0078413 A1* | 4/2008 | Padget .................. A61L 15/42 128/849 |
| 2008/0083495 A1 | 4/2008 | Sher |
| 2009/0187130 A1 | 7/2009 | Asmus |
| 2011/0132213 A1 | 6/2011 | DeJoseph |

FOREIGN PATENT DOCUMENTS

| | | |
|---|---|---|
| JP | 7-125404 | 5/1995 |
| JP | 8-299418 | 11/1996 |
| JP | 11-502840 | 3/1999 |
| JP | 2005-502386 | 1/2005 |
| JP | 2008-95057 | 4/2008 |
| JP | 2008-206577 | 9/2008 |
| JP | 2010-209190 | 9/2010 |
| WO | WO 89/07429 | 8/1989 |
| WO | WO 01/58698 | 8/2001 |
| WO | WO 02/13980 | 2/2002 |
| WO | WO 2006/020708 A2 | 2/2006 |
| WO | WO 2010/056541 | 5/2010 |
| WO | WO 2010/056543 | 5/2010 |

* cited by examiner

METHOD OF MAKING PRESSURE-SENSITIVE ADHESIVE ARTICLE INCLUDING ACTIVE AGENT

FIELD

The present disclosure relates broadly to pressure-sensitive adhesive articles and methods for their manufacture.

BACKGROUND

Wound care articles such as, for example, wound dressings and incise drapes are available in a variety of designs to protect wounds and surgical incisions from infection. Such articles are commonly adhered to the skin of patients by a pressure-sensitive adhesive (PSA) layer. Typically, the PSA layer is disposed on a substrate such as a flexible film, foam, woven materials, non-woven materials, or gauze. To reduce risk of infection, antimicrobial material (e.g., material including an antimicrobial compound) has been used in combination with the PSA layer.

SUMMARY

In one aspect, the present disclosure provides a method of making a pressure-sensitive adhesive article, the method comprising:

contact printing an active composition onto a surface of a release substrate to form a printed surface, whereby the active composition spontaneously dewets the surface of the release substrate to form active deposits on the surface of the release substrate, wherein the active composition comprises an active agent dissolved or dispersed in an aqueous liquid vehicle; and disposing a pressure-sensitive adhesive layer on the printed surface.

Methods according to the present disclosure are useful; for example, to prepare adhesive articles having active agents incorporated therein.

Non-contact methods such as inkjet printing may be unreliable for some fluid solutions due to problems such as nozzle clogging and/or corrosion, and can be relatively slow.

Advantageously, methods according to the present disclosure are effective for depositing biologically active compositions on a pressure-sensitive adhesive, without the aforementioned problems associated with inkjet printing. Additionally, they may be useful with flimsy substrates, where other printing methods may not be effective.

As used herein:

The term "active agent" refers to a compound or combination of compounds that act locally on the tissue of a mammal to prevent, reduce, or cure a condition. In some embodiments, the active agent comprises pharmacologically-effective compound or combination of compounds. Active agents may or may not be present at pharmaceutically and/or clinically effective amounts.

The term "aqueous" means containing at least 5 percent by weight of water.

The term "contact printing" refers to any printing or coating process in which a composition is in simultaneous contact with a printing or metering element and the surface of the release substrate, and is urged against the surface of the release substrate by the printing or metering element.

The terms "dewet" and "dewetting" refer to a spontaneous process that occurs at a solid-liquid interface, and refer to contraction and/or rupture of a thin liquid film on the surface of the release substrate. The process is an opposite process to spontaneous spreading of a liquid on the release substrate.

The term "hydratable polymer" refers to a polymer that is water-soluble, water-swellable, and/or water erodible at a temperature in a range of from 20° C. to 40° C.

The term "release substrate" refers to a substrate that releasably adheres to and readily separates from a pressure-sensitive adhesive material without substantial adhesive transfer.

The term "rounded" means substantially shaped into the form of a circle or sphere; made round.

The features and advantages of the present disclosure will be further understood upon consideration of the detailed description as well as the appended claims.

It should be understood that numerous other modifications and embodiments can be devised by those skilled in the art, which fall within the scope and spirit of the principles of the disclosure. The figures may not be drawn to scale. Like reference numbers may have been used throughout the figures to denote like parts.

DETAILED DESCRIPTION

Figure 1:
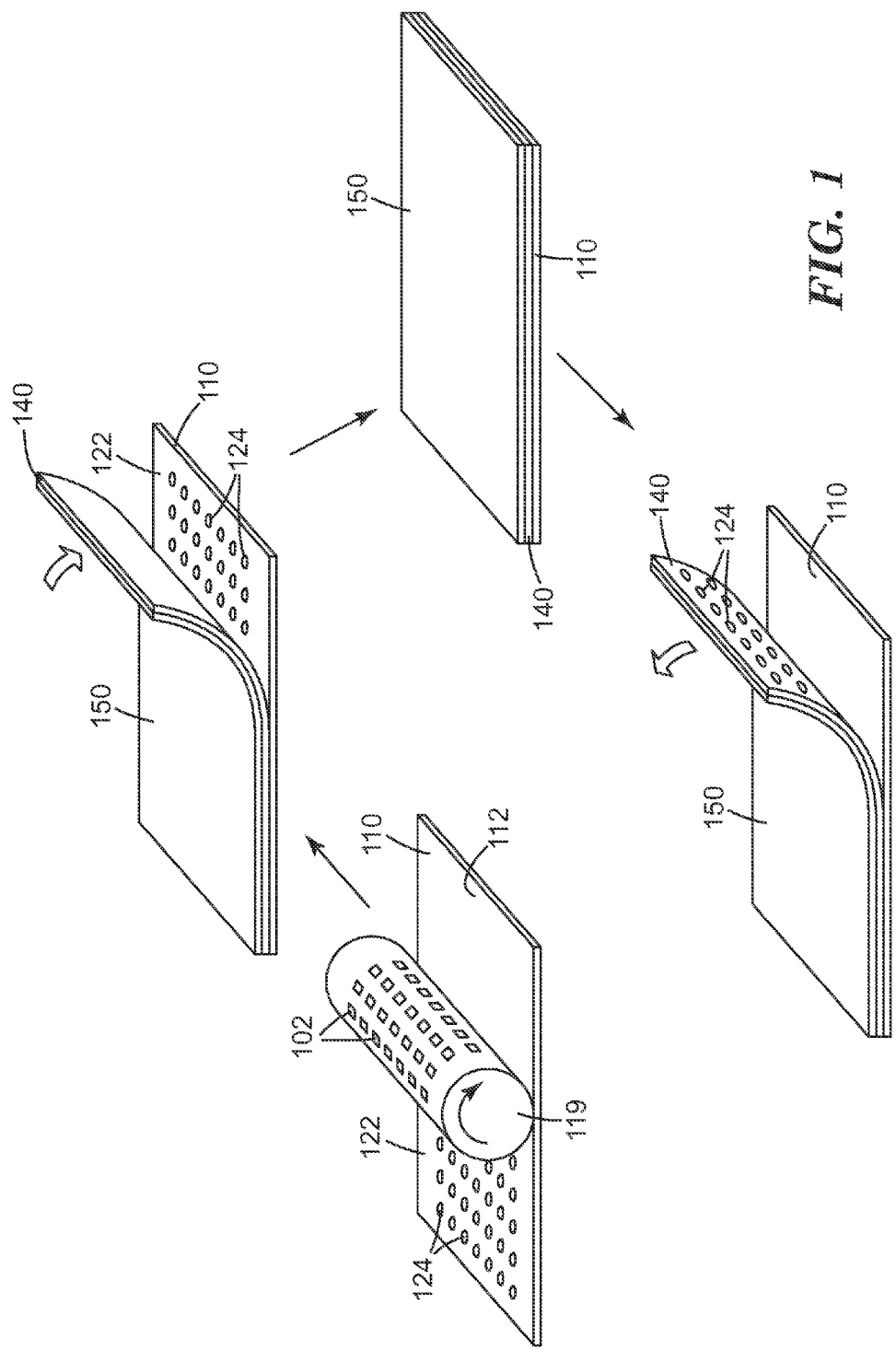
FIG. 1 is a schematic process flow diagram of an exemplary method according to the present disclosure.

Referring now to FIG. 1, one exemplary method of making a pressure-sensitive adhesive article according to the present disclosure comprises contact printing an active composition 102 on contact printing roll 119 onto surface 112 of release substrate 110. Active composition 102 comprises an active agent dissolved or dispersed in an aqueous liquid vehicle. Once printed, the active composition spontaneously dewets surface 112 to form active deposits 124 on surface 112 to form printed surface 122. Pressure-sensitive adhesive layer 140, supported on backing 150, is then disposed on printed surface 122 by lamination. Subsequent separation of printed surface 122 from pressure-sensitive adhesive layer 140 results in transfer of active deposits 124 to pressure-sensitive adhesive layer 140.

Figure 2:
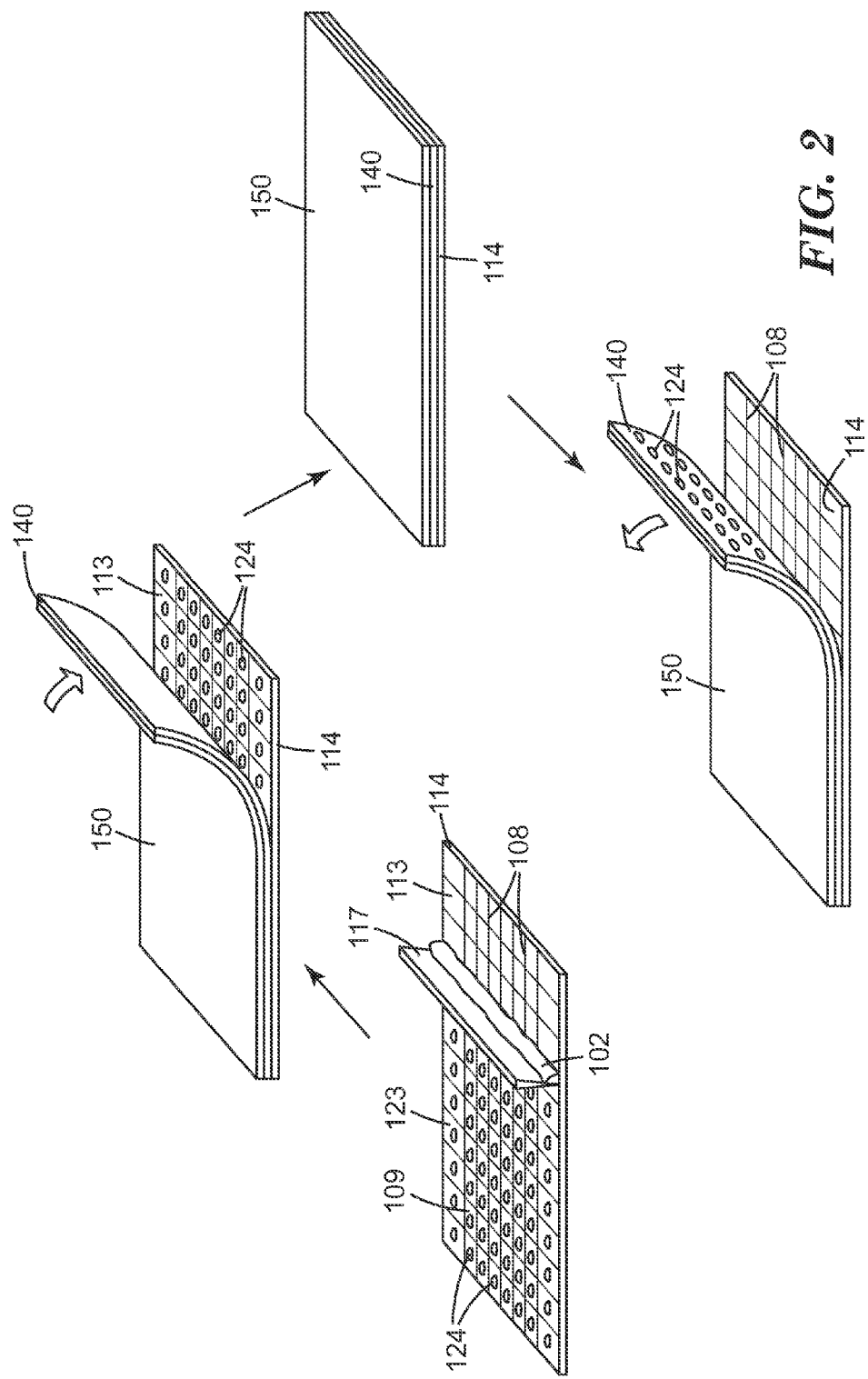
FIG. 2 is a schematic process flow diagram of another exemplary method according to the present disclosure.

Referring now to FIG. 2, another exemplary method of making a pressure-sensitive adhesive article according to the present disclosure comprises contact printing active composition 102 onto structured surface 113 of release substrate 114 using knife coater 117. Structured surface 113 includes ridges 108. Once printed, active composition 102 spontaneously dewets structured surface 113 to form active deposits 124 surrounded by ridges 108 (e.g., in corners and/or centers of recessed areas 109 surrounded by ridges 108 depending on the viscosity of the active composition) to form printed surface 123. Next, backing 150 having layer of pressure-sensitive adhesive layer 140 disposed thereon is laminated to printed surface 123. Subsequent separation of printed surface 123 from pressure-sensitive adhesive layer 140 results in transfer of active deposits 124 to pressure-sensitive adhesive layer 140.

In other embodiments, the pressure-sensitive adhesive layer may be disposed on the printed surface by a solvent coating process, and then the backing is laminated onto the pressure-sensitive adhesive layer.

Useful contact printing methods include, for example, flexography, roll coating, knife-coating, doctor-blade coating, and gravure roll coating. Of these techniques, flexography is particularly desirable.

An advantage of using contact printing as opposed to non-contact printing methods such as spraying or jetting methods is that breathable airborne droplets (e.g., containing a biologically active agent) present in the vicinity of the printing apparatus are greatly reduced or eliminated.

Figure 3:
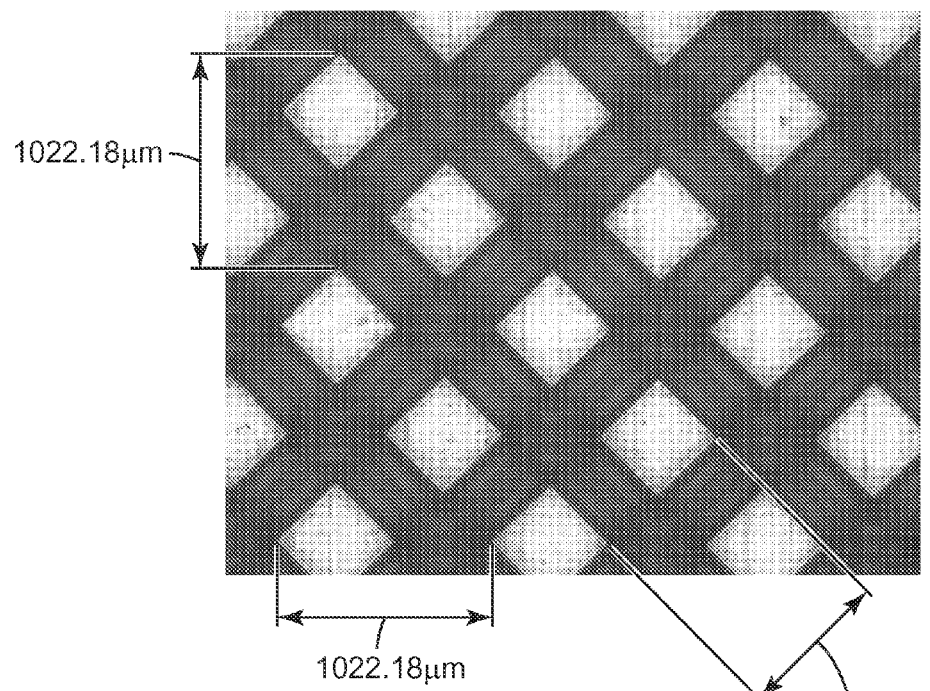
FIG. 3 is a photomicrograph of the flexographic printing plate used in Example 1d.

The active composition may be contact printed onto the surface of the release substrate according to any pattern or image. Examples of patterns include combinations and arrays comprising dots, squares, diamonds, lines, circles, hexagons, triangles, and combinations thereof. For example, a flexographic printing plate as shown in FIG. 3 can be used to print active compositions, which after shrinkage of the inked area and drying results in an array of active deposits as shown, for example, in FIG. 4 or FIG. 5, depending on the composition. The pitch (or spacing) of a printed array of active deposits may range, for example, from 0.1 microns to 1 centimeter, or more.

The active composition comprises an active agent and an aqueous liquid vehicle. In some embodiments, the active composition further comprises a hydratable polymer. Combinations of active agent, and/or hydratable polymers may be included in the active compositions and active deposits.

Exemplary useful active agents (e.g., therapeutics) include: herbal medicines, anti-inflammatory drugs, both steroidal (e.g., prednisolone, triamcinolone) and nonsteroidal (e.g., naproxen, piroxicam); antibacterials (e.g., penicillins, cephalosporins, erythromycin, tetracycline, gentamycin, sulfathiazole, nitrofurantoin, trimethoprim, and quinolones (e.g., norfloxacin, flumequine, and ibafloxacin), bacitracin and its salts, neomycin and its salts, polymixin B) and antiseptics (e.g., chlorhexidine, chlorhexidine gluconate, alexidine, octenidine, antimicrobial quaternary ammonium surfactants such as benzalkonium chloride, cetylpyridinium chloride, and cetyltrimethylammonium halides, phenols, cresols, triclosan, antibacterial natural oils, iodophors, quaternary ammonium compounds, protonated tertiary and secondary amine compounds, certain metal ions (e.g., silver, and copper) and their salts (e.g., silver gluconate, silver lactate, and silver sulfate), biguanides, triclosan, and polymeric antibacterials (e.g., polyhexamethylene biguanide, polymers having protonated primary, secondary and/or tertiary amines, and polyquaternary amines), antimicrobial lipids such as those described in U.S. Publ. Pat. Appln. No. 2005/0089539 A1 (Scholz et al.), which include the $C_8$-$C_{12}$ alkyl monoesters and monoethers of glycerin and propylene glycol; antiprotazoals (e.g., metronidazole); cardiovascular pharmaceuticals (e.g., amlodipine besylate, nitroglycerin, nifedipine, losartan potassium, irbesartan, diltiazem hydrochloride, clopidogrel bisulfate, digoxin, abciximab, furosemide, amiodarone hydrochloride, beraprost, theophylline, pirbuterol, salmeterol, isoproterenol, and tocopheryl nicotinate); calcium channel blockers (e.g., nifedipine, diltiazem); enzyme inhibitors such as collagenase inhibitors, protease inhibitors, elastase inhibitors, lipoxygenase inhibitors (e.g., A64077), and angiotensin converting enzyme inhibitors (e.g., captopril, lisinopril); other antihypertensives (e.g., propranolol); leukotriene antagonists (e.g., ICI204, 219) antiulceratives such as H2 antagonists; steroidal hormones (e.g., progesterone, testosterone, estradiol, levonorgestrel, mycophenolate mofetil, and methylprednisolone); antivirals and/or immunomodulators (e.g., 1-isobutyl-1H-imidazo[4,5-c]quinolin-4-amine, 1-(2-hydroxyl-2-methylpropyl)-1H-imidazo[4,5-c]quinoline-4-amine, acyclovir); cardiotonics (e.g., digitalis, digoxin); antitussives (e.g., codeine, dextromethorphan); antihistamines (e.g., diphenhydramine, chlorpheniramine, terfenadine); exfoliants (e.g., alpha-hydroxy acids or beta-hydroxy acids); analgesics (e.g., tramadol hydrochloride, fentanyl, metamizole, ketoprofen, morphine sulfate, lysine acetylsalicylate, acetaminophen, ketorolac tromethamine, morphine, loxoprofen sodium, and ibuprofen); dermatological products (e.g., isotretinoin and clindamycin phosphate); anesthetics (e.g., propofol, midazolam hydrochloride, and lidocaine hydrochloride); migraine therapies (e.g., ergotamine, melatonin, sumatriptan, zolmitriptan, and rizatriptan); sedatives and hypnotics (e.g., zolpidem, zolpidem tartrate, triazolam, and hycosine butylbromide); imaging components (e.g., iohexyl, technetium, TC99M, sestamibi, iomeprol, gadodiamide, ioversol, and iopromide); peptide hormones (e.g., human or animal growth hormones LHRH); cardioactive products such as atriopeptides; proteinaceous products (e.g., insulin); enzymes (e.g., anti-plague enzymes, lysozyme, dextranase), antinauseants (e.g., scopolamine); anticonvulsants (e.g., carbamazepine); immunosuppressives (e.g., cyclosporine); psychotherapeutics (e.g., diazepam, sertraline hydrochloride, venlafaxine, bupropion hydrochloride, olanzapine, buspirone hydrochloride, alprazolam, methylphenidate hydrochloride, fluvoxamine maleate, and ergoloid mesylates); sedatives (e.g., phenobarbital); anticoagulants (e.g., heparin); analgesics (e.g., acetaminophen); antimigraine agents (e.g., ergotamine, melatonin, sumatriptan); cholesterol reducers (e.g., atorvastatin calcium, lovastatin, bezafibrate, ciprofibrate, and gemfibrozil); antiarrhythmic agents (e.g., flecamide); antiemetics (e.g., metoclopramide, ondansetron); blood modifiers (e.g., epoetin alfa, enoxaparin sodium, and antihemophilic factor); antiarthritic components (e.g., celecoxib, nabumetone, misoprostol, and rofecoxib); AIDS and AIDS-related pharmaceuticals (e.g., lamivudine, indinavir sulfate, and stavudine); diabetes and diabetes-related therapies (e.g., metformin hydrochloride, insulin, troglitazone, and acarbose); biologicals (e.g., hepatitis B vaccine, and hepatitis A vaccine); immune response modifiers (e.g., purine derivatives, adenine derivatives, and CpGs); anticancer agents (e.g., methotrexate, paclitaxel, carboplatin, tamoxifen citrate, docetaxel, epirubicin hydrochloride, leuprolide acetate, bicalutamide, goserelin acetate implant, irinotecan hydrochloride, gemcitabine hydrochloride, and sargramostim); gastrointestinal products (e.g., lansoprazole, ranitidine hydrochloride, famotidine, ondansetron hydrochloride, granisetron hydrochloride, sulfasalazine, and infliximab); respiratory therapies (e.g. loratadine, fexofenadine hydrochloride, cetirizine hydrochloride, fluticasone propionate, salmeterol xinafoate, and budesonide); immunosuppressives (e.g., cyclosporine); neurologic agents such as anxiolytic drugs; hemostatics; anti-obesity agents; nicotine; algicides; and pharmaceutically acceptable salts and esters of the foregoing.

Active agents may be selected from those that are non-reactive with the pressure-sensitive adhesive layer and/or other components of the active composition, although reactive active agents may be used. Antimicrobial active agents are typically selected based on the type of microorganisms the adhesive articles will encounter in a particular use. Typically, the active is non-volatile, although this is not a requirement. The active agent may be included in the active composition in any amount. In some embodiments, the active agent may be present in an amount of at least 10, 20, 30, 40, or even at least 50 percent by weight, based on the total weight of the active composition.

In some embodiments, it may be desirable to add one or more excipients for transdermal drug transport to the active composition to produce transdermal drug delivery vehicles. Excipients are compounds that serve to assist or retard the diffusion of the pharmaceutical across a membrane. Examples of excipients include: terpenes (e.g., alpha-terpineol, (+)-terpinen-4-ol, 1,3,3-trimethyl-2-oxabicyclo[2.2.2] octane, p-cymene); alcohols including polyols (e.g., (S)-(+)-2,2-dimethyl-1,-3-dioxolane-4-methanol, (R)-(−)-2,2-dimethyl-1,3-dioxolane-4-methanol, 1,2-propanediol, butane-1,3-diol, diethylene glycol monoethyl ether, tetrahydrofurfuryl alcohol polyethylene glycol ether, ethylene glycol, ethanol, propanol, glycerol); esters (e.g., propylene glycol laurate, isopropyl myristate, isopropyl palmitate, ethylhexyl palmitate, butyl dodecanoate, lauric acid lauryl ester, propanoic acid 2-hydroxy-dodecyl ester, linoleic acid butyl ester, lauric acid methyl ester, methyl dodecanoate, dodecyl dodecanoate, lauric acid methyl ester, methyl dodecanoate, lauric acid ethyl ester, ethyl dodecanoate, oleic acid ethyl ester, (−)-methyl L-lactate, ethyl lactate, lauryl lactate, butyl lactate); amides (e.g., N,N-dimethylformamide, N,N-dimethylacetamide, N-laurylpyrrolidone, N-octylpyrrolidone, N-(2-hydroxyethyl)pyrrolidone, N-methylpyrrolidone, 1-dodecylazacycloheptan-2-one and other N-substituted alkylazacycloalkyl-2-ones); halocarbons (e.g., chloroform, methylene chloride); fatty acids (e.g., lauric acid, oleic acid, isostearic acid, linoleic acid, capric acid, neodecanoic acid); cationic, anionic, and nonionic surfactants (e.g., sodium dodecyl sulfate, polyoxamers); anticholinergic agents (e.g., benzilonium bromide, oxyphenonium bromide), oils (e.g., tea tree oil, mineral oil), ketones (e.g., acetone), ethers (e.g., tetrahydrofuran); dimethyl sulfoxide; acetonitrile; aqueous solvents (e.g., water, buffered saline, Lactated Ringer's), and combinations thereof.

Active compositions according to the present disclosure typically include from about 0.01 to about 100 percent by weight of the active agent, more typically 0.1 to 80 percent by weight exclusive of volatile co-solvents (e.g., ethanol, isopropanol) based on the total weight of the active composition, although other amounts may be used. In the case of chlorhexidine gluconate, the active composition typically includes from about 1 to about 70 percent by weight of chlorhexidine gluconate, based on the total weight of the active composition, although other amounts can also be used. In general, the amount of active agent to include will be influenced by the activity of the selected active agent and the intended application. For example, the active deposits may comprise from 20 to 100 percent of active agent, although other amounts may also be used.

Hydratable polymers used in the present invention may be cationic, non-ionic, anionic, or zwitterionic, and may be optionally modified with hydrophobic groups. Suitable hydratable polymers may be linear, branched, or crosslinked (e.g., water-swellable polymers).

Hydratable polymers that are slightly-crosslinked may be water-swellable. If introduced chemically, the concentration of crosslinker is generally quite low, e.g., less than about 1000 ppm, or less than 500 ppm, based on the weight of the dry polymer. Water-swellable polymers can also be prepared using chemical crosslinkers, and/or ionizing radiation may be used to crosslink. For examples, polymers comprising N-vinyl lactams, such as N-vinyl pyrrolidone, when exposed to gamma radiation increase in molecular weight and may actually crosslink.

Examples of cationic hydratable polymers include both permanently charged quaternary polymers (those polymers comprising quaternary amines such polyquaternium polymers and in particular polyquaternium 4, 7, 10, 24, 32, and 37) as well as protonated primary, secondary, and tertiary amine functional polymers which have been protonated with a suitable protonic acid.

Protonated cationic polymers may be protonated with suitable acids that will not result in undue skin irritation such as $C_1$-$C_{10}$ alkylcarboxylic acids optionally substituted by oxygen (e.g., acetic acid, alpha hydroxyacids such as lactic acid, gluconic acid, and the like), $C_1$-$C_{10}$ alkylsulfonic acids (e.g., methylsulfonic acid and ethylsulfonic acid), $C_1$-$C_{10}$ alkylhydrogensulfates (e.g., methylhydrogensulfate) and mineral acids (e.g., hydrochloric acid, hydrobromic acid, sulfuric acid, and phosphoric acid). The charge on protonated cationic polymers is pH dependent. For this reason, in order to ensure the polymer is sufficiently protonated, the pH must be adjusted appropriately, and should generally be in the range of 5-9.5, desirably 6.5-7.5. Representative classes of polymers include: cationic polysaccharides, cationic homopolymers and copolymers derived from acrylic and/or methacrylic acid, cationic cellulose guar and other gum resins, cationic copolymers of dimethyldiallylammonium chloride and acrylamide and or acrylic acid, cationic homopolymers of dimethyldiallylammonium chloride, cationic polyalkylene and ethoxypolyalkylene imines, and combinations thereof.

Exemplary cationic hydratable polymers include: cationic guar gums such as hydroxypropyl trimethyl ammonium guar gum (d.s. of from 0.11 to 0.22) available from Rhodia, Cranberry, N.J. as JAGUAR C-14-S and JAGUAR C-17, and also JAGUAR C-16, which contains hydroxypropyl substituents (d.s. of from 0.8-1.1) in addition to the above-specified cationic groups; quaternized hydroxyethyl cellulose ethers available as UCARE POLYMER JR-30M and JR-400 (Amerchol Corporation, Edison, N.J.) and CELQUAT (National Starch and Chemicals Corp., Bridgewater, N.J.); which are copolymers of a polyethoxylated cellulose and dimethyldiallylammonium chloride and has the Cosmetic, Toiletry and Fragrance Association (CTFA) designation Polyquaternium-4. Other suitable cationic polymers are homopolymers of dimethyldiallylammonium chloride available as MERQUAT 100 (Nalco Co., Naperville, Ill.), copolymers of dimethylaminoethyl methacrylate and acrylamide, copolymers of dimethyldiallylammonium chloride and acrylamide, available commercially under the trade designations MERQUAT 550 and Merquat S (Nalco Co.), acrylic acid/dimethyldiallylammonium chloride/acrylamide copolymers available under the trade designation MERQUAT 3330 (Nalco Co.), quaternized vinylpyrrolidone acrylate or methacrylate copolymers of amino alcohol, Polyquaternium 11, 23 and 28 (quaternized copolymers of vinylpyrrolidone and dimethylaminoethyl methacrylate-GAFQUAT 755N (International Specialty Products, Wayne, N.J.) and quaternized copolymers of vinyl pyrrolidone and dimethylaminoethyl methacrylamide-HS-100), vinyl pyrrolidone/vinyl imidazolium methochloride copolymers available as LUVIQUAT FC370 (BASF Corp., Florham Park, N.J.), Polyquaternium 2, polyalkylenimines such as polyethylenimine and ethoxylated polyethylenimine, and alkyl modified quaternary ammonium salt of hydroxyethyl cellulose and a trimethylammonium chloride substituted epoxide available as Polyquaternium 24, available as QUATRISOFT LM-200 from Amerchol Corp., Edison, N.J.

Exemplary non-ionic hydratable polymers include: polyalkylene oxides (e.g., polyethylene oxide, polypropylene oxide, and random and block copolymers of ethylene oxide, propylene oxide, and butylene oxide including those available under the trade designation POLYOX from Dow Chemical Co., Midland, Mich.); cellulosics such as hydroxyethyl cellulose and hydroxypropylmethyl cellulose, methylhydroxypropyl cellulose (e.g., available as BENECEL MP 943 from Aqualon, Wilmington, Del.), hydroxypropyl cellulose (e.g., available as KLUCEL (LF, GF, MF, HF) from Aqualon, hydroxybutylmethyl cellulose (3.5% hydroxybutyl and 30% methoxyl, available from Scientific Polymer Products, Ontario, N.Y.); polyacrylamides; polyvinyl alcohols (e.g., derived from polyvinyl acetate having 40-100%, desirably 85-100%, hydrolysis including those available under the trade designations POVAL from Kuraray Co., Tokyo, Japan, ELVANOL from E.I. du Pont de Nemours and Co., Wilmington, Del.); polyvinyl pyrrolidones (e.g., those available under the trade designations PVP-Kxx from Peakchem, ZheJiang, China, where the "xx" number after the letter "K" indicates the average molecular weight in 1,000 s of Daltons of the polymer such as PVP-K90 and PVP-K30); starch, dextran; xanthan gums, hydrophilic polyurethanes such as ethoxylated and sulfonated polyurethanes; copolymers of methyl vinyl ether and maleic anhydride (e.g., as available under the trade designation GANTREZ from International Specialty Products, Wayne, N.J.); plant exudates such as acacia, ghatti, and tragacanth; other natural polysaccharide polymers such as guar gum, locust bean gum, and xanthan gum, and karaya gum. These polymers may be optionally hydrophobically modified (e.g., NATROSOL PLUS hydrophobically modified hydroxyethyl cellulose from Ashland, Covington, Ky.).

Exemplary anionic hydratable polymers include acrylic acid/ethyl acrylate copolymers and carboxyvinyl polymers marketed by B. F. Goodrich Co., Akron, Ohio, under the trade designation CARBOPOL. These resins consist essentially of a colloidally water-swellable polyalkenyl polyether crosslinked polymer of acrylic acid crosslinked with from 0.75% to 2.00% of a crosslinking agent such as for example polyallyl sucrose or polyallyl pentaerythritol. Examples include CARBOPOL 934, CARBOPOL 940, CARBOPOL 950, CARBOPOL 980, CARBOPOL 951) and CARBOPOL 981. CARBOPOL 934 is a water-swellable polymer of acrylic acid crosslinked with about 1 percent of a polyallyl ether of sucrose having an average of about 5.8 allyl groups for each sucrose molecule. Also suitable are hydrophobically-modified cross-linked polymers of acrylic acid having amphipathic properties available as CARBOPOL 1382, CARBOPOL 1342 and PEMULEN TR-1 (CTFA Designation: Acrylates/10-30 Alkyl Acrylate Crosspolymer, from Lubrizol, Wickliffe, Ohio). Anionic polymers also may be formed having sulfate or sulfonate groups such as polymers derived from 2-acrylamido-2-methylpropanesulfonic acid (AMPS). Anionic polymers also may be based on natural polymers such as carboxymethylcellulose and seaweed extracts such as sodium alginate, propylene glycol alginate and sodium carrageenan.

Examples of zwitterionic hydratable polymers include proteins such as gelatin, polybetaines, polysultaines, and polyamine oxides.

Suitable hydratable polymers may have a wide range of molecular weights, where the molecular weight and amount generally strongly influence viscosity of the active composition determines the product performance. For example, if the polymer molecular weight is too high, the active composition may be too viscous to print effectively using a chosen technique. Alternatively, if the molecular weight of the polymer is too low and/or the amount of the hydratable polymer is too small, the active composition may not be sufficiently viscous to print effectively on the release substrate using a chosen technique.

The total amount of hydratable polymers present in the active composition is typically in a range of from 1 to 15 percent by weight, more typically in a range of from 1 to 10 percent by weight, based on the total weight of the active composition, although lesser and greater amounts may also be used. In general, the amount of hydratable polymer to include will be influenced by the printing technique selected and the chemical composition of the hydratable polymer(s).

The aqueous liquid vehicle comprises at least 5 percent by weight of water, and may comprise at least 10, 20, 30, 40, 50, 60, or even 70 percent by weight of water, or more. The aqueous liquid vehicle may also comprise co-solvents that form a single phase with the water. Examples of suitable co-solvents include water miscible solvents such as methanol, ethanol, isopropanol, ethylene glycol, propylene glycol, acetone, glyme, acetonitrile, diglyme, N,N-dimethylformamide, dioxane, glycerol, and combinations thereof. Examples of suitable water-soluble, immiscible co-solvents include tetrahydrofuran, dimethyl sulfoxide, and diethylene glycol. The co-solvents may be used in any amount, typically though they are selected such that they form a single liquid phase. Some high-boiling solvents such as, for example, ethylene glycol, propylene glycol, glyme, diglyme, N,N-dimethylformamide, dioxane, and glycerol may also serve as plasticizers and/or swelling agents.

The active compositions may further comprise one or more additional additives such as, for example, thixotropes, thickeners including inorganic thickeners such as, e.g., silica gel, laponite, and bentonite, ultraviolet light (UV) stabilizers, antioxidants, adjuvants, fragrances, and colorants.

Suitable release substrates may include, for example, those release substrates which are suitable for use with pressure-sensitive adhesives. Examples of suitable release substrates include conventional release substrates comprising a material such as, for example, a polyester film, a polyolefin (e.g., polyethylene, polypropylene) film, paper, or a film-coated paper laminate such as a polyethylene-coated paper. These release substrates may be coated with a low surface energy fluoropolymer-based, silicone-based, or acrylic-based polymer coating. Typically, the surface of the release substrate on which the active composition is printed has a critical surface tension (or surface energy) less than or equal to that of linear polyethylene. The low surface energy coating may be applied to one or both major surfaces and may or may not be crosslinked.

The release substrate may include kraft paper, polyethylene, polypropylene, polyester, or composite of any of these materials, typically coated with a release agent such as fluorochemicals or silicones. For example, U.S. Pat. No. 4,472,480 (Olson) describes low surface energy perfluorochemical release substrates. Examples of commercially available silicone-coated release substrate include POLYSLIK silicone release papers from Loparex LLC, Hammond, Wis., and silicone release papers supplied by Daubert Chemical Co., Dixon, Ill. While typically not necessary, it is envisaged that the release substrate used in practice of methods according to the present disclosure may be removed and replaced by another, different release substrate. The release substrate may comprise, for example, a sheet, belt, web, or roll.

In some embodiments, the release substrate may comprise a structured surface (i.e., a structured release substrate). Typically, the microstructure surface comprises a repeating pattern or array of raised features. The raised features may comprise, for example, right prisms (e.g., triangular prisms, square prisms, or hexagonal prisms), regular prisms, truncated square pyramids, posts, ridges, grooves, or a combination thereof. The raised features may comprise a combination of heights and/or shapes. Typically, the raised features have a height in a range of from 5 to 500 microns, more typically from 5 to 75 microns, although other heights may also be used. Structured release substrates are well known in the adhesive arts. In some embodiments, the active composition is printed on the raised features; for example by roll coating. Alternatively, in some embodiments, the active composition is printed on one or more areas of the low energy surface disposed between the raised features (e.g., land area); for example, by knife or bar coating, followed by squeegeeing away excess active composition.

Further details concerning structured release substrates and methods for their fabrication may be found in, for example, U.S. Patent Appl. Publ. Nos. 2006/0127626 A1 (Fleming et al.), 2007/0039271 A1 (Fleming et al.); and 2008/0083495 A1 (Sher et al.).

Typically, the active composition has a surface tension sufficiently large to cause the active composition, after contact printing onto the surface of the release substrate, to shrink with respect to its initial contact area with the release substrate. Such area shrinkage may be at least 10, 20, 30, 40 50, 60, or 70 percent, or more. During shrinkage the profile of the ink becomes more drop-like.

Any portion, or all, of the low energy surface of the release substrate may be printed with the active composition. In order to ensure sufficient adhesive properties of the pressure-sensitive adhesive layer after contacting the printed surface of the release substrate, the active deposits may cover less than 15 percent, less than 12 percent, or less than 7 percent of the total area of the low energy surface, although other coverage amounts may also be used. In order to achieve efficacy of the active agent, the active deposits typically cover at least 2 percent, at least 3 percent, at least 4 percent of the total area of the low energy surface, although other coverage amounts may also be used.

In terms of the resulting pressure-sensitive adhesive article, the active deposits may cover less than 15 percent, less than 12 percent, or less than 7 percent of the total area of the outer major surface (i.e., opposite the release substrate) of the pressure-sensitive adhesive layer, although other coverage amounts may also be used.

After contact printing onto the release substrate, the active composition may be at least partially dried (e.g., substantially dried or completely dried) by at least partial removal of the liquid vehicle, although this is not a requirement. After such drying, one or more of the thickness and average diameter may typically decrease somewhat although the active deposits retain a rounded appearance. Drying may be effected by evaporation optionally with heating. Examples of heat sources include ovens, heated rolls and platens, and infrared heaters.

In typical contact printing processes, the ink and a substrate are chosen such that the ink generally wets the substrate to allow it to stay where it is deposited during printing. The present disclosure typically involves printing a relatively high surface tension (and surface energy) aqueous active composition onto a relatively low surface energy (relative to the active composition) surface of a release substrate. Accordingly, the aqueous active composition typically does not spontaneously spread across the surface of the release substrate (i.e., it does not wet the substrate well). The inventors have presently discovered that this de-wetting tends to cause the exact pattern of the original printed image (e.g., corresponding to a flexographic plate) to be lost as the patterning fluid de-wets resulting in active deposits, which depending on the original printing pattern may have nearly uniform size, and can be placed according to controlled patterns (e.g., see FIGS. 4 and 5). Without wishing to be bound by theory, the success of this controlled de-wetting seems to be influenced by the patterning fluid having the proper viscosity and surface tension. At thick viscosities, de-wetting occurs only slowly or not at all, while at very thin viscosities, contact printing may be difficult to achieve. In general, good printing and de-wetting is observed for active compositions having a viscosity in a range of from 50 centipoise (cP) (50 mPa-sec) to 2500 cP (2500 mPa-sec), desirably in a range of from 100 cP (100 mPa-sec) to 1000 cP (1000 mPa-sec) as measured using a using a BROOKFIELD viscometer (Model DV-II+, Brookfield Engineering Laboratories, Middleboro, Mass.), at 23° C. according to the manufacturer's instructions, although other viscosities may also be used.

After contact printing (and optional removal of at least a portion of the aqueous liquid vehicle), the thickness and surface coverage of the resulting active deposits will typically depend on the intended use. Thus, for applications such as, for example, incise drapes, the active deposits may have a thickness in a range of from 0.1 to 100 microns, more typically in a range of from 1 to 55 microns, or even in a range of from 10 to 50 microns, although other thickness ranges may also be used. For example, the active deposits may have a thickness of at least 0.1, 0.5, 1, 2, 5, 10, 15, 20, 25, 30 40, 50, 60, 75, 100, 150, or even at least 200 microns, or more.

The pressure-sensitive layer comprises a polymer that can be used as the basis for a pressure-sensitive adhesive. It is desirably dermatologically and pharmaceutically acceptable (e.g., medical grade), and substantially chemically inert to the chosen active agent. Examples of suitable polymers include: acrylates such as those disclosed, for example, in U.S. Pat. No. RE 24,906 (Ulrich), U.S. Pat. No. 3,389,827 (Abere et al.), U.S. Pat. No. 4,112,213 (Waldman), U.S. Pat. No. 4,310,509 (Berglund et al.), U.S. Pat. No. 4,732,808 (Krampe et al.), U.S. Pat. No. 4,737,410 (Kantner), U.S. Pat. No. 5,876,855 (Wong et al.), and U.S. Pat. No. 7,097,853 (Garbe et al.); polyisobutylenes; polyisoprenes; styrene block copolymers (e.g., SEBS copolymers, SBS copolymers); and silicones as disclosed in U.S. Pat. No. 5,232,702 (Pfister), and PCT International Application Publications WO 2010/056541A1 (Liu et al.) and WO 2010/056543 A1 (Liu et al.). Inclusion of medicaments or antimicrobial agents in the pressure-sensitive adhesive is also contemplated; for example, as described in U.S. Pat. No. 4,310,509 (Berglund et al.) and U.S. Pat. No. 4,323,557 (Rosso et al.).

Acrylic pressure-sensitive adhesives generally have a glass transition temperature of about −20° C. or less, and may comprise from 100 to 80 weight percent of a $C_3$-$C_{12}$ alkyl ester component such as, for example, isooctyl acrylate, 2-ethylhexyl acrylate and n-butyl acrylate and from 0 to 20 weight percent of a polar component such as, for example, acrylic acid, methacrylic acid, acrylamide, ethylene vinyl acetate, N-vinylpyrrolidone and styrene macromer. In some embodiments, the acrylic pressure-sensitive adhesives comprise from 0 to 20 weight percent of acrylic acid and from 100 to 80 weight percent of isooctyl acrylate. Certain active agents (e.g., CHG) may react with acrylic acid, and pressure-sensitive adhesives containing acrylamide or N-vinylpyrollidone instead of acrylic acid may be desirable in such instances.

The pressure-sensitive adhesive layer desirably transmits moisture vapor at a rate greater than or equal to that of human skin, although this is not a requirement. While such a characteristic can be achieved through the selection of an appropriate adhesive, other methods of achieving a high relative rate of moisture vapor transmission may be also used; for example, pattern coating the adhesive on the backing, as described in U.S. Pat. No. 4,595,001 (Potter et al.). The adhesive may be applied to selection regions of the backing or release substrate in a continuous or discontinuous manner.

Useful pressure-sensitive adhesives may further include an elastomeric material. Examples of suitable elastomeric materials include linear, radial, star and tapered styrene-isoprene block copolymers such as KRATON D 1107P from Shell Chemical Co., Houston, Tex. and EUROPRENE SOL TE 9110 from EniChem Elastomers Americas, Inc., Houston, Tex.; linear styrene-(ethylene-butylene) block copolymers such as KRATON G1657, available from Shell Chemical Co.; linear styrene-(ethylene-propylene) block copolymers such as KRATON G1657X, available from Shell Chemical Co.; linear, radial, and star styrene-butadiene block copolymers such as KRATON D 1118X, available from Shell Chemical Co.; and EUROPRENE SOL TE 6205, available from EniChem Elastomers Americas, Inc.; polyetheresters such as HYTREL G3548, available from DuPont; and poly-a-olefin-based thermoplastic elastomeric materials such as those represented by the formula —($CH_2$ CHR), where R is an alkyl group containing 2 to 10 carbon atoms and poly-$\alpha$-olefins based on metallocene catalysis such as ENGAGE EG8200, an ethylene/poly-$\alpha$-olefin copolymer available from Dow Plastics Co. of Midland, Mich.; natural rubbers such as CV-60, a controlled viscosity grade, and SMR-5, a ribbed smoked sheet rubber; butyl rubbers, such as EXXON BUTYL 268 available from Exxon Chemical Co.; synthetic polyisoprenes such as CARIFLEX IR309, available from Royal Dutch Shell of Netherlands and NAT-SYN 2210, available from Goodyear Tire and Rubber Co.; ethylene-propylenes; polybutadienes; polyisobutylenes such as VISTANEX MM L-80, available from Exxon Chemical Co.; and styrene-butadiene random copolymer rubbers such as AMERIPOL 1011A, available from BF Goodrich of Akron, Ohio.

Pressure-sensitive adhesives may be self-tacky or tackified. Useful tackifiers for acrylic polymers include rosin esters such as FORAL 85 from Hercules, Inc. of Wilmington, Del., aromatic resins such as PICCOTEX LC-55WK from Hercules, Inc., and aliphatic resins such as ESCOREZ 1310LC from Exxon Chemical Co of Houston, Tex. Tackifiers, if present, typically comprise from about 5 to 75 percent by weight of the pressure-sensitive adhesive.

Useful pressure-sensitive adhesives may be crosslinked or non-crosslinked.

The pressure-sensitive adhesive may cover all or only a portion of the major surface of the backing, and it may be uniformly coated to form a film substantially free of voids or it may be pattern coated. Pattern coating may be used, for example, to increase moisture vapor transmission.

In addition, other additives such as colorants, fillers, waxes, plasticizers, and antioxidants may be included in the pressure-sensitive adhesive layer.

Typically, the pressure-sensitive layer is about 10 to 600 microns thick, more typically 20 to 60 microns thick, although other thicknesses may also be used. The acrylic pressure-sensitive adhesive layer may be disposed on the release substrate or the backing, for example, using melt extrusion techniques, coating polymerizable adhesive precursor material and then radiation-curing (e.g., e-beam and/or ultraviolet light), by lamination, or by solvent coating.

The backing should be capable of supporting the pressure-sensitive layer. In some embodiments, the backing has a substantially smooth major surface, is flexible, and is optionally conformable. Examples of useful backings include nonwoven fabrics, polymer films, and metal foils. The backing may, for example, comprise a web, belt, roll, or sheet.

Useful backings include, for example, flexible films and nonwovens. Examples of materials that may be used in the flexible films and nonwovens include polyolefins (e.g., polyethylenes, polypropylenes, polybutylenes, and metallocene polyolefins such as polyolefin elastomers available under the trade designation ENGAGE, and polyolefin plastomers available under the trade designation AFFINITY, from Dow Chemical Co., Midland, Mich.), polyesters (e.g., those available under the trade designation HYTREL from E.I. du Pont de Nemours & Co., Wilmington, Del.), polyamides, styrene/butadiene copolymers (e.g., those available under the trade designation KRATON from Kraton Polymers, Houston Tex.), and polyurethane elastomers (e.g., those polyurethane elastomers available under the trade designations ESTANE 5701, ESTANE 58309, ESTANE 58237, and ESTANE 5702); rayon, chloroprene rubber, ethylene/propylene rubbers, polybutadiene rubber, polyisoprene rubber, natural or synthetic rubber, butyl rubber, silicone rubber, or EPDM rubber; and combinations thereof. In some embodiments, the backing comprises a high moisture vapor permeable film; for example, as described in U.S. Pat. No. 3,645,835 (Hodgson) and U.S. Pat. No. 4,595,001 (Potter et al.). In some embodiments, the backing and pressure-sensitive adhesive layer may be obtained as a composite article (i.e., with the pressure-sensitive layer disposed on the backing). One such useful composite article, a polyurethane elastomer film coated on one side with pressure-sensitive adhesive, is commercially available from 3M Company under the trade designation TEGADERM.

The backing is desirably readily conformable to anatomical surfaces, although this is not a requirement. As such, when applied to an anatomical surface, it conforms to the surface even when the surface is moved, and can stretch and retract. In some embodiments, the backing comprises an elastomeric polyurethane film, polyester film, or polyether block amide film.

In methods according to the present disclosure, the release substrate printed with active composition (i.e., printed release substrate) is urged against the pressure-sensitive adhesive layer, typically disposed on a backing (e.g., a film or sheet), optionally with sufficient force that at least a portion of the plurality of active deposits becomes at least partially embedded in the pressure-sensitive adhesive layer. Pressure may be applied by any suitable method such as, for example, using a cold roll laminator, nip rolls, a press, or hand-pressure. In some embodiments, at least a portion of the plurality of active deposits becomes fully embedded in the pressure-sensitive adhesive. Fully embedded active deposits may be flush with the outer surface or embedded below the outer surface of the pressure-sensitive adhesive layer. In some embodiments, at least a portion of the plurality of active deposits are sufficiently embedded that they contact the backing.

In embodiments wherein the backing is highly compliant and prone to damage during web handling, the pressure-sensitive adhesive layer may be alternatively disposed onto the printed release substrate and then the resultant assembly is laminated to the backing in a subsequent step. Advantageously, this method is typically effective for manufacture of incise drapes, which typically have a highly compliant and difficult to handle backing layer.

While the active deposits may be essentially flush with the outer major surface of the pressure-sensitive adhesive layer, it is also within the scope of the present disclosure to have active deposits overfill corresponding recesses and be disposed partially above the outer major surface. Likewise, active deposits may only partially fill corresponding recesses.

Antimicrobial pressure-sensitive adhesive articles according to the present disclosure are useful. For example they may be applied to skin and used as incise drapes, tapes, wound dressings (e.g., including occlusive dressings and pressure dressings), and transdermal patches. In the case of a tape, pressure-sensitive adhesive articles according to the present disclosure can have a low adhesion backsize disposed on a major surface of a backing opposite the adhesive layer, and the backing and pressure-sensitive adhesive layer (with active deposits thereon) can be wound upon itself to form a roll.

Objects and advantages of this disclosure are further illustrated by the following non-limiting examples, but the particular materials and amounts thereof recited in these examples, as well as other conditions and details, should not be construed to unduly limit this disclosure.

EXAMPLES

Unless otherwise noted, all parts, percentages, ratios, etc. in the Examples and the rest of the specification are by weight.

The following materials were used in the Examples that follow.

TABLE OF MATERIALS

| DESCRIPTION | SOURCE |
|---|---|
| 2-phenoxyethanol | Sigma Aldrich, St. Louis, Missouri |
| ARISTOFLEX HMB | Clariant, Charlotte, North Carolina |
| Benzoic Acid, product number 36230 | Alfa Aesar, Ward Hill, Massachusetts |
| BRIJ-78 surfactant, stearyl alcohol ether of polyoxyethylene with an average of 20 repeat units (POE(20)), Catalog Number S-320 | ChemService, Inc., West Chester, Pennsylvania |
| Butterfield's buffer, BPPFV9BFD, product no. 70-2007-5075-3 | 3M Company, Saint Paul, Minnesota |
| Chlorhexidine gluconate (CHG), 20 percent weight/volume solution in water | Xttrium Laboratories, Inc., Chicago, Illinois |
| COSMOCIL CQ polyhexamethylenebiguanide (PHMB) | Arch Personal Care Products, Norwalk, Connecticut |
| Structured Release Substrate 1: ridges per inch = 20 (7.9 ridges/cm), sidewall slope = 90 degrees, width at base = 90-100 microns (μm), height = 28 μm | prepared as described in WO 02/13980 |
| Structured Release Substrate 2: height = 25 μm, side wall slope from plane = 10 degrees, pitch = 292 μm, gap between pyramids = 6 μm, tops of pyramids = 2 μm | prepared as described in US 2003/0017291 A1 |
| Guar, Stock # G4129 | Sigma Aldrich, St. Louis, Missouri |
| Hexadecylpyridinium chloride, Product Number H0078 | TCI America, Portland, Oregon |
| Hydroxypropyl cellulose $M_w$~100,000, Stock Number 191884 | Sigma Aldrich |
| HYTREL 4056 film, a polyester elastomer film, extruded from HYTREL 4056 resin | E. I. du Pont de Nemours & Co., Wilmington, Delaware |
| LAURICIDIN monolaurin | Med-Chem Laboratories, Inc., Goodyear, Arizona |
| Methicillin Resistant *Stapyhlococcus Aureus* (MRSA), ATCC #33592 | American Type Culture Collection (ATCC), Manassas, Virginia |
| Octenidine-HCl | Dishman, Ahmedabad, India |
| PEG-4000 (polyethylene glycol), Ph Eur standard. Product Number 8.7006.5000 | EMD Chemicals, Darmstadt, Germany |
| Polyvinyl alcohol - High Molecular Weight (PVA-HMW), 87-89 percent hydrolyzed, average M.W. = 88,000-97,000 g/mol, product no. 41240 | Alfa Aesar |
| Polyvinyl alcohol - Low Molecular Weight (PVA-LMW), 87-89 percent hydrolyzed, average M.W. = 10,000 to 26,000 g/mol, product no. 41238 | Alfa Aesar |
| Polyvinyl pyrrolidone (PVP HMW), $M_w$~10,000 g/mol, Stock Number 85,645-2 | Sigma-Aldrich |
| *Pseudomonas Aeroginosa*, ATCC #9027, | American Type Culture Collection (ATCC) |
| Red dye, 0.1 percent red food coloring | McCormick & Co., Sparks, Maryland |
| Red Pigment, D&C Red 30 Lake on Talc, 6730 | Clark Colors, Inc., South Plainfield, New Jersey |
| RITA PCMX chloroxylenol | Rita Corporation, Crystal Lake, Illinois |
| SENSIVA SC 50 ethylhexyl glycerin | Schulke & Mayr, Norderstedt, Germany |
| Siliconized paper substrate, R296550858, 60#//3000SF | Mondi Coatings, Vienna, Austria |
| 1720 siliconized film substrate, a platinum-catalyzed, thermally-cured silicone release substrate on polypropylene film | Huhtamaki, Forchheim, Germany |
| 1752 siliconized film substrate, a platinum-catalyzed, thermally-cured silicone release substrate on polypropylene film | Huhtamaki |

TABLE OF MATERIALS

| DESCRIPTION | SOURCE |
| --- | --- |
| SOFTCAT SK-MH polymer | Amerchol, Edison, New Jersey |
| *Staphylococcus Epidermidis*, ATCC #1222 | American Type Culture Collection (ATCC) |
| STERI-DRAPE 1050 incise drape, Part No. 70-2004-1797-3 | 3M Company |
| TWEEN 20 polyoxyethylenesorbitan monolaurate | MP Biomedicals, Solon, Ohio |
| TEGADERM 1624W transparent dressing | 3M Company |

Preparation of Acrylic Release Substrate

Isostearyl acrylate (NK ESTER ISA, Osaka Organic Chemical Industry Ltd., Osaka, Japan), stearyl acrylate (NK ESTER STA, Osaka Organic Chemical Industry, Ltd.) and EBECRYL P36 (Cytec Industries, West Paterson, N.J.), in monomer ratio of 50/50/0.4, were suspended in a blend of 50:50 ethyl acetate/heptanes to a solids content of 60 percent by weight. This mixture was charged to a reactor vessel. Then 0.3 parts of initiator V-601 (2,2'-azobis(2-methylpropionate), Wako Pure Chemical Industries, Ltd., Osaka, Japan) was charged, followed by purging the contents of the vessel with nitrogen gas for 10 minutes. The vessel was sealed and placed in a rotary constant-temperature bath maintained at 50° C. The reaction was allowed to proceed for 24 hrs.

The resulting copolymer solution was diluted to 2 percent by weight with a solvent mix of toluene/2-butanone (50:50) and the diluted solution was then coated, using a #4 wire-wound rod, onto a 2 mils (51 microns) thick polyester film (F7S, Toray Plastics America, North Kingstown, R.I.). The coated film was then irradiated under a high-pressure mercury vapor lamp (H bulb, 130 W/cm; Fusion Systems Corporation, Gaithersburg, Md.) by passing twice, at 40 fpm (12 m/min), under nitrogen, with UVA energy density of 506 mJ/cm$^2$, to yield the acrylic release substrate film.

Examples 1-9

Printing Formulation #1

A 20% w/w aqueous solution of PVA (High Molecular Weight) was prepared by stirring the PVA/water mixture at elevated temperature for several days. After cooling, 350 grams of this solution was mixed with 150 grams of 20% CHG solution. 0.1% red dye was added. The Brookfield viscosity of this solution at room temperature was 140 cP (140 mPa-sec, #31 spindle, 30-100 rpm range).

Printing Formulation #2

163 grams of the 20% PVA (High Molecular Weight) solution described for Printing Formulation #1 was mixed with 163 grams of 20% CHG solution and 174 grams of water. 0.1% red dye was added. The Brookfield viscosity of this solution at room temperature was 190 cP (190 mPa-sec, #31 spindle, 30-100 rpm range).

Printing Formulation #3

75 grams of the 20% PVA (High Molecular Weight) solution described for Printing Formulation #1 was mixed with 176 grams of 20% CHG solution and 250 grams of water. 0.1% red dye was added. The Brookfield viscosity of this solution at room temperature was 200 cP (200 mPa-sec, #31 spindle, 30-100 rpm range).

Printing Formulation #4

A solution of 19% w/w PVA (44-51 percent hydrolyzed, $M_n$=93,000 g/mol; $M_w$=400,000 g/mol) (150 grams)) in methanol was mixed with 160 grams of 20% CHG solution and 190 grams of water. 0.1% red dye was added. The Brookfield viscosity of this solution at room temperature was 140 cP (140 mPa-sec, #31 spindle, 30-100 rpm range).

Printing Formulation #5

A dispersion of 5% w/w Guar in water was prepared by stirring the mixture with heat for several days. 164 grams of this dispersion was mixed with 155 grams of 20% CHG solution and 232 grams of water. 0.1% red dye was added. The Brookfield viscosity of this solution at room temperature was 200 cP (200 mPa-sec, #31 spindle, 10-50 rpm range).

Printing Formulation #6

75 grams of the 5% guar dispersion prepared for Printing Formulation #5 was mixed with 350 grams of 20% CHG solution and 285 grams of water. 0.1% red dye was added. The Brookfield viscosity of this solution at room temperature was 700 cP (700 mPa-sec, #31 spindle, 10 rpm).

Printing Formulation #7

350 grams of the PVA (High Molecular Weight) solution prepared for Printing Formulation #1 was mixed with 150 grams of 20% CHG solution and 0.1% red dye was added to prepare a CHG/PVA stock solution. 200 grams of 20% CHG solution was diluted with 467 grams of water and 0.1% red dye was added to prepare a CHG stock solution. 207 grams of the CHG/PVA stock solution was mixed with 84 grams of the CHG stock solution to produce the final printing formulation. The viscosity (Norcross method) of this solution at room temperature was 920 cP (920 mPa-sec).

Printing Formulation #8

10 parts of a sample of Printing Formulation #7 was diluted with 1 part of the CHG stock solution as described for Printing Formulation #7. The viscosity (Norcross method) of this solution at room temperature was 640 cP (640 mPa-sec).

Printing Formulation #9

10 parts of a sample of Printing Formulation #8 was diluted with 1 part of the CHG stock solution as described for Printing Formulation #7. The viscosity (Norcross method) of this solution at room temperature was 420 cP (420 mPa-sec).

Viscosity Measurements

Unless otherwise indicated, viscosities of the printing formulations were measured using a BROOKFIELD viscometer (Model DV-II+, Brookfield Engineering Laboratories, Middleboro, Mass.). The viscometer was equipped with spindle #31 or spindle #21. The tests were done at room temperature.

The viscosities of Printing Formulations 7-9 were measured with Norcross viscosity measuring cups (Norcross Corporation, Newton, Mass.). For Printing Formulations 7 and 8, Norcross shell cup number 5 was placed into a large plastic beaker, filled with the desired solution and allowed to sit for a few minutes to allow for dissipation of any air bubbles. The cup was then lifted allowing the solution to drain. The time it took to drain was recorded and the viscosity determined from a standardized graph supplied by Norcross. For Printing Formulation 9, the same procedure was followed, except Norcross cup number 4 was used.

Examples 1-9

For each of Printing Formulations 1a-1d (replicates) and Printing Formulations 2-9, a rolling bank of the Printing Formulation was maintained on an anilox roll by manually adding the Printing Formulation just ahead of the doctor blade, as needed. The anilox roll then metered the solution onto a printing roll. The pattern of the printing roll was a square array of raised square pads, each with an area of about 0.14 mm$^2$, as shown in FIG. 3. The center-to-center distance between adjacent squares was approximately 0.7 mm along the two mutually orthogonal square grid directions, and about 1.0 mm along a diagonal.

Figure 4:
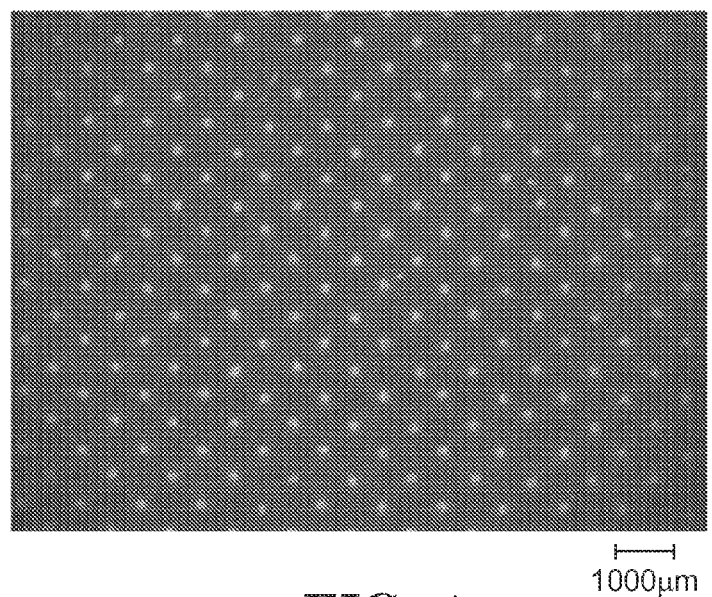
FIG. 4 is a photomicrograph of the Printed Release Substrate 1d.
Figure 5:
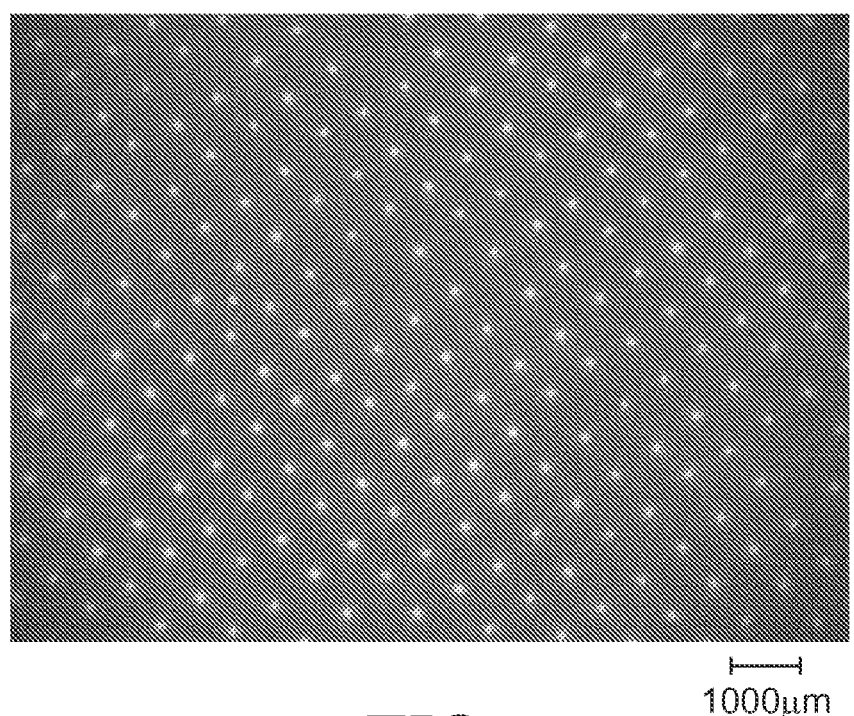
FIG. 5 is a photomicrograph of the Printed Release Substrate 5.

The printing roll was then used to apply the printing formulation to a siliconized paper substrate, with the substrate moving at 10 feet per minute. The substrate bearing the wet pattern was then passed through an oven 10 feet long to dry the pattern. For the pattern of Printed Release substrate 1, drying was performed at four different oven temperatures, and the four specimens are designated Printed Release Substrates 1a-1d in Table 1. The dried pattern on each substrate was imaged with fluorescence microscopy. FIG. 4 shows the fluorescence micrograph for the dried pattern on substrate of Printed Release Substrate 1d. FIG. 5 shows the fluorescence micrograph for the dried pattern on substrate of Printed Release Substrate 5. As typified by FIGS. 4 and 5, each exemplary printed release substrate bore a pattern of circular spots corresponding to the locations of the mixture of CHG and polymer. The spacing of the spots matched well the spacing of the features in the printing roll pattern (i.e., approximately 0.7 mm between spots in a square array). Analysis of these images determined the percent area coverage of the pattern on the substrate and the median area of the individual spots. In Table 1 (below), the area coverage numbers were taken from images of two different samples of the pattern, and the median spot size is the median from the combined data from both images.

TABLE 1

| EXAMPLE | OVEN TEMPERATURE, ° C. | PERCENT AREA COVERAGE | MEDIAN SPOT AREA, mm$^2$ | SPOT AREA/ PAD AREA |
| --- | --- | --- | --- | --- |
| 1a | 75 | 2.5, 2.7 | 0.013 | 0.09 |
| 1b | 90 | 2.7, 3.1 | 0.013 | 0.09 |

TABLE 1-continued

| EXAMPLE | OVEN TEMPERATURE, ° C. | PERCENT AREA COVERAGE | MEDIAN SPOT AREA, mm$^2$ | SPOT AREA/ PAD AREA |
| --- | --- | --- | --- | --- |
| 1c | 105 | 2.7, 2.8 | 0.013 | 0.09 |
| 1d | 120 | 2.9, 3.1 | 0.015 | 0.11 |
| 2 | 75 | 2.5, 2.8 | 0.013 | 0.09 |
| 3 | 75 | 2.1, 3.1 | 0.013 | 0.09 |
| 4 | 75 | 1.6, 2.8 | 0.009 | 0.06 |
| 5 | 75 | 1.7, 1.9 | 0.009 | 0.06 |
| 6 | 75 | 1.4, 1.7 | 0.008 | 0.06 |
| 7 | 75 | 2.3, 2.4 | 0.010 | 0.07 |
| 8 | 75 | 2.4, 2.5 | 0.013 | 0.09 |
| 9 | 75 | 2.7, 3.4 | 0.015 | 0.11 |

Adhesion Testing for CHG Incise Drape Formulation

Specimens of the printed release substrates from Printing Formulations 1d, 5, 6, and 9 were hand-coated with an isooctyl acrylate/N-vinylpyrrolidone (IOA/NVP, 91/9) adhesive. A coating weight of approximately 11 grains (0.713 grams) per 155 cm$^2$ was targeted. The adhesive-coated specimens were then dried at 82° C. in an oven for approximately 3 to 5 minutes. Each of the dried specimens was then laminated to a sheet of HYTREL 4056 linerless film. Lamination was performed by passing the substrate bearing adhesive and the backing together through non-heated rollers, with the adhesive side facing the HYTREL 4056 film. To assess these specimens, adhesion to steel was performed as follows. Book tape (SCOTCH 845 book repair tape, 3M Company) was adhered to the HYTREL 4056 film side of a drape specimen. Then, a strip 1.0 inch (2.5 cm) wide and approximately 4 to 6 inches (10 to 15 cm) long was cut from the specimen. A pull handle was fashioned from masking tape, and was attached to one end of the 1.0 inch (2.5 cm) strip. The strip was then adhered to a #302 or 304 AISI stainless steel plate with bright annealed finish, freshly cleaned with a solution of heptane/isopropyl alcohol (1 to 1 ratio, wt./wt.), by removing the release substrate, and carefully laying down the tape strip, and rolling up and down once with a 4.5 pound roller. A 180-degree peel test was performed per ASTM Test Method D1000-10 "Standard Test Methods for Pressure-Sensitive Adhesive-Coated Tapes Used for Electrical and Electronic Applications" at a speed of 12 inches/minute (30 cm/min) The average peel force was recorded. The test was run in triplicate for each specimen.

Typical peel force values for some commercially available incise drapes are slightly above 24 oz/in width (0.27 kg/cm width). The results in Table 2 (below) show that Examples 1d, 9, 5, and 6 indicates that CHG patterning on the surface of the adhesive did not negatively impact peel adhesion.

TABLE 2

| EXAMPLE | Pull 1, oz/in (kg/cm) | Pull 2, oz/in (kg/cm) | Pull 3, oz/in (kg/cm) | Mean, oz/in (kg/cm) | Standard Deviation, oz/in (kg/cm) |
| --- | --- | --- | --- | --- | --- |
| 1d | 28.5 (0.32) | 31.2 (0.35) | 33.7 (0.32) | 31.1 (0.35) | 2.6 (0.03) |
| 5 | 37.2 (0.42) | 38.6 (0.43) | 41.0 (0.46) | 38.9 (0.43) | 1.9 (0.02) |
| 6 | 36.4 (0.41) | 39.8 (0.43) | 38.1 (0.43) | 38.1 (0.43) | 1.7 (0.02) |
| 9 | 24.3 (0.27) | 33.7 (0.32) | 29.4 (0.32) | 29.1 (0.32) | 4.7 (0.05) |

Time Kill Testing of Antimicrobial Performance

Specimens of several Examples used in the adhesion testing above were also subjected to antimicrobial performance testing. A 5-minute time kill study was performed as follows.

A suspension of methicillin resistant *Staphylococcus aureus* (MRSA, ATCC #33592) was prepared at a concentration of $1 \times 10^8$ CFU (colony forming units) per milliliter (mL) in phosphate buffered water (pbw) using a 0.5 McFarland Equivalence Turbidity Standard. Using an Eppendorf pipette, 50 μL of this suspension was transferred as 15-16 separate droplets to the adhesive surface of a 2.5 cm diameter section of the adhesive film. These inoculated specimens were then incubated at room temperature (23+/−2° C.) for 5 minutes. After incubation, the specimens were placed in 20 mL of neutralizing buffer and sonicated for one minute followed by vortexing for two minutes. Portions of the resulting solution were serially diluted with pbw. The neat solution and dilutions were each plated to 3M PETRIFILM aerobic count plates (3M Company) and incubated for at least 24 hours. The 3M PETRIFILM plates were then counted using a 3M PETRIFILM plate reader (model 6499, 3M Company). Examples 1d, 5, and 9 each showed a log reduction of from 2 to 3. No log reduction was found for a control (placebo) specimen utilizing an otherwise comparable non-patterned substrate.

Testing with TEGADERM Adhesive Formulation

The release substrate was removed from specimens of TEGADERM 1624W transparent dressing. Then using a roller, each specimen was hand-laminated onto a CHG patterned substrate selected from among Examples 1d, 5, and 6 in Table 1. The laminates were then cut to fit the 1624W dressing. These laminate specimens were used for the Antimicrobial Zone of Inhibition (ZOI) tests and other testing.

Antimicrobial Zone of Inhibition (ZOI) Testing

Antimicrobial performance was quantitatively determined using a zone of inhibition test.

A solution of *Staphylococcus epidermidis* and *Pseudomonas aeroginosa* was prepared using a 0.5 McFarland Turbidity Standard at a concentration of approximately $1 \times 10^8$ colony forming units per milliliter in Butterfield's Buffer. For each specimen to be tested, a bacterial lawn was prepared by dipping a sterile cotton applicator into the solution and swabbing a dry surface of a Mueller Hinton II plate in three different directions. An 8 millimeters (mm) diameter disc cut from the adhesive sheet to be tested was then placed onto the plate and pressed firmly to ensure a complete contact with the plate. The plate was held in an incubator at 35±2° C. for 24 hours. A measurement was then made of the diameter of the area around each sample (including the area under the 8-mm diameter sample disc) where inhibited growth and/or no growth was observed. The zone of inhibition diameter was recorded in terms of the primary zone of inhibition. The primary zone of inhibition was defined as the diameter of the area within which no growth was observed (including the area under the 8-mm diameter sample disk). Results are reported in Table 3. Some tests were replicated, and in those cases, both results are shown. All specimens exhibited a zone of inhibition. The TEGADERM 1624W transparent dressing specimens exhibited slightly larger zone of inhibition than comparable IOA/NVP specimens. The large increase in concentration of CHG in Example 1d did not lead to proportionately larger zone of inhibition values. The PVA samples (Examples 1d and 9) exhibited slightly better zone of inhibition than the guar samples (Examples 5 and 6).

TABLE 3

| | | | Zone Size, mm | | | | | |
|---|---|---|---|---|---|---|---|---|
| | | CHG, percent by weight in coated printing | No Aging | | Aged 60° C. for 2 weeks | | Aged 40° C./75 percent R.H. for 2 weeks | |
| EXAMPLE | ADHESIVE | formulation | Staph. | Pseudo. | Staph. | Pseudo. | Staph. | Pseudo. |
| 5 | TEGADERM 1624W | 6 | 19 | 8 | | | | |
| 6 | TEGADERM 1624W | 6 | 18 | 8 | | | 18 | 13 |
| 1d | TEGADERM 1624W | 14 | 22 | 11 | 22 | 17 | 23 | 16 |
| 1d | IOA/NVP | 14 | 21 | 10 | | | | |
| 1d | IOA/NVP | 14 | 21 | 9 | | | | |
| 9 | IOA/NVP | 6 | 20 | 8 | | | | |
| 9 | IOA/NVP | 6 | 20 | 8 | | | | |
| 5 | IOA/NVP | 6 | 18 | 8 | | | | |
| 5 | IOA/NVP | 6 | 18 | 8 | | | | |
| 6 | IOA/NVP | 6 | 17 | 8 | | | | |
| 6 | IOA/NVP | 6 | 17 | 8 | | | | |

Examples 10-17

Examples 10-17 show the effects of varying the printing plate pattern.

Printing Plate Pattern 1

Printing plate pattern 1 had individual elevated areas of square shape 0.30 mm on each side corresponding to an elevated pad area of about 0.090 mm². The square areas were arranged in a square array with a center-to-center distance of 0.63 mm.

Printing Plate Pattern 2

Printing plate pattern 2 had individual elevated areas of square shape 0.29 mm on each side corresponding to an elevated pad area of about 0.084 mm². The square areas were arranged in a square array with a center-to-center distance of 2.9 mm.

Printing Plate Pattern 3

Printing plate pattern 3 had individual elevated areas of circular shape of 0.18 mm diameter corresponding to an elevated pad area of about 0.025 mm². The circular areas were arranged in a hexagonal array with a center-to-center distance of 0.24 mm.

Printing Plate Pattern 4

Printing plate pattern 4 had individual elevated areas of circular shape of 0.09 mm diameter corresponding to an elevated pad area of about 0.006 mm². The circular areas were arranged in a hexagonal array with a center-to-center distance of 0.17 mm.

Example 10

A printing formulation was prepared by first dissolving 25% w/w PVA (low MW) in water using heat and several days of stirring. The PVA solution (610 grams) was mixed with 286.3 grams of 20% CHG solution and 56.7 grams of water and 0.4% red pigment was added. The resulting printing formulation had a Brookfield viscosity at room temperature of 460 cP (460 mPa-sec, #31 Spindle, 50 rpm) and a pH of 5.2. It was patterned onto a siliconized paper substrate using printing plate pattern 1. The resulting pattern had area coverage of 4.0 percent with a median spacing between patterned spots of about 0.6 mm and median spot size of about 0.024 mm².

Example 11

The printing formulation used in Example 10 was patterned onto a siliconized paper substrate using printing plate pattern 2. The resulting pattern had area coverage of 2.1% percent with a median spacing between patterned spots of about 2.6 mm and median spot size of about 0.123 mm².

Example 12

A printing formulation was prepared by mixing 459 grams of a 20% PVA (High molecular weight) solution identical to that in Example 1 with 351 grams of 20% CHG solution, 24 grams of PEG-4000, and 337 grams of water. Red pigment (0.4%) was added. The printing formulation had a Brookfield viscosity at room temperature of 480 cP (480 mPa-sec, #31 Spindle, 50 rpm) and a pH of 4.8. It was patterned onto a siliconized paper substrate using printing plate pattern 1. The resulting pattern had area coverage of 3.1 percent with a median spacing between patterned spots of about 0.6 mm and median spot size of about 0.012 mm².

Example 13

The printing formulation from Example 12 was patterned onto a siliconized paper substrate using printing plate pattern 2. The resulting pattern had area coverage of 0.9% percent with a median spacing between patterned spots of about 2.7 mm and median spot size of about 0.030 mm².

Example 14

A printing formulation was prepared by dissolving 100 grams of PVP HMW in 400 grams of 20% CHG solution by stirring at room temperature overnight. Red dye (0.1 percent) was added. The printing formulation had a Brookfield viscosity at room temperature of 160 cP (160 mPa-sec, #21 spindle, 3-12 rpm range) and a pH of 4.8. It was patterned onto siliconized polymer substrate 1752 using printing plate pattern 3. The resulting pattern had area coverage of 2.6 percent with a median spacing between patterned spots of about 0.24 mm and a median spot size of 0.0019 mm².

Example 15

The printing formulation from Example 14 was patterned onto a 1752 siliconized film substrate using printing plate pattern 4. The resulting pattern had area coverage of 2.9 percent with a median spacing between patterned spots of about 0.17 mm and a median spot size of 0.0006 mm².

Example 16

A printing formulation was prepared by dissolving 17.5 grams of hydroxypropyl cellulose in 487.5 grams of 20% CHG solution by stirring at room temperature overnight. Red dye (0.1 percent) was added. It had a Brookfield viscosity at room temperature of 210 cP (210 mPa-sec, #21 Spindle, 12 rpm) and a pH of 4.6. It was patterned onto a 1752 siliconized film substrate using printing plate pattern 3. The resulting pattern had area coverage of 1.5 percent with a median spacing between patterned spots of about 0.24 mm and a median spot size of 0.0005 mm².

Example 17

The printing formulation from Example 16 was patterned onto a siliconized paper substrate using printing plate pattern 4. The resulting pattern had area coverage of 1.5 percent with a median spacing between patterned spots of about 0.17 mm and a median spot size of 0.0004 mm².

Examples 18-30

Examples 18-30 show the effects of further varying the printing formulation and substrate.

Method for Preparing Examples 18-30

Double-coated tape was used to mount the printing plate shown in FIG. 3 onto a brass disk with a 114 mm diameter and 51 mm width. A number 20 Meyer rod (RD Specialties, Webster, N.Y.) was used to coat a layer of printing formulation onto a plate of glass. The brass disk with the printing plate was rolled across the coated glass and then immediately rolled onto a release substrate. The substrate was placed in a 100° C. oven for between 1 and 5 minutes.

Example 18

A printing formulation was prepared by mixing 8.2 grams of a 20% PVA (High molecular weight) solution identical to that in Example 1 with 0.4 grams of LAURICIDIN, 0.8 grams of BRIJ 78, 0.03 grams of benzoic acid, and 10.6 grams of water. 0.4% of red pigment was added, and the solution was stirred at room temperature. It was coated onto a siliconized surface of a siliconized-paper substrate as described above. The resultant printed surface was laminated to a piece of STERI-DRAPE 1050 incise drape (Part no. 70-2004-1797-3, 3M Company). The adhesive was peeled from the siliconized-paper substrate, and the pattern transferred to the adhesive with coverage of 4.0 percent by area. The median distance between spots was about 0.6 mm and the median spot size was about 0.019 mm².

Example 19

A printing formulation was prepared by mixing 8.2 grams of a 20% PVA (High molecular weight) solution identical to that in Example 1 with 0.4 grams of SENSIVA SC 50, 0.8 grams of BRIJ 78, 0.03 grams of benzoic acid, and 10.6 grams of water. 0.4% of red pigment was added, and the solution was stirred at room temperature. It was coated onto a siliconized surface of a siliconized-paper substrate as described above. The resultant printed surface was laminated to a piece of STERI-DRAPE 1050 incise drape. The adhesive was peeled from the siliconized-paper substrate, and the pattern transferred to the adhesive with coverage of 2.8 percent by area. The median distance between spots was about 0.6 mm and the median spot size was about 0.012 mm$^2$.

Example 20

A printing formulation was prepared by mixing 8.2 grams of a 20% PVA (High molecular weight) solution identical to that in Example 1 with 6 grams of COSMOCIL CQ and 5.8 grams of water. 0.4% of red pigment was added, and the solution was stirred at room temperature. It was coated onto a siliconized surface of a paper substrate as described above. The resultant printed surface was laminated to a piece of STERI-DRAPE 1050 incise drape. The adhesive was peeled from the substrate, and the pattern transferred to the adhesive with coverage of 2.6 percent by area. The median distance between spots was about 0.6 mm and the median spot size was about 0.010 mm$^2$.

Example 21

A printing formulation was prepared by mixing 8.2 grams of a 20% PVA (High molecular weight) solution identical to that in Example 1 with 0.2 grams of hexadecylpyridinium chloride and 11.6 grams of water. 0.4% of red pigment was added, and the solution was stirred at room temperature. It was coated onto a siliconized surface of a paper substrate as described above. The resultant printed surface was laminated to a piece of STERI-DRAPE 1050 incise drape. The adhesive was peeled from the substrate, and the pattern transferred to the adhesive with coverage of 1.8 percent by area. The median distance between spots was about 0.6 mm and the median spot size was about 0.010 mm$^2$.

Example 22

A printing formulation was prepared by mixing 8.2 grams of a 20% PVA (High molecular weight) solution identical to that in Example 1 with 0.2 grams of RITA PCMX and 11.6 grams of water. 0.4% of red pigment was added, and the solution was stirred at room temperature. It was coated onto a siliconized surface of a paper substrate as described above. The resultant printed surface was laminated to a piece of STERI-DRAPE 1050 incise drape. The adhesive was peeled from the substrate, and the pattern transferred to the adhesive with coverage of 0.9 percent by area. The median distance between spots was about 0.6 mm and the median spot size was about 0.005 mm$^2$.

Example 23

A printing formulation was prepared by mixing 8.2 grams of a 20% PVA (High molecular weight) solution identical to that in Example 1 with 0.4 grams of Octenidine-HCl and 11.4 grams of water. 0.4% of red pigment was added, and the solution was stirred at room temperature. It was coated onto a siliconized surface of a paper substrate as described above. The resultant printed surface was laminated to a piece of STERI-DRAPE 1050 incise drape. The adhesive was peeled from the substrate, and the pattern transferred to the adhesive with coverage of 7.6 percent by area. The median distance between spots was about 0.6 mm and the median spot size was about 0.022 mm$^2$.

Example 24

A printing formulation was prepared by magnetically stirring 50 grams of 20% CHG solution under vacuum in a round bottom flask in a 60° C. oil bath for 30 minutes, during which time the solution weight decreased to 23.7 grams. 23.0 grams of this solution was stirred under similar heat and vacuum for an additional 10 minutes, during which time the weight decreased to 16.4 grams. 14.8 grams of this solution was diluted with 1.2 grams of water. This solution had a Brookfield viscosity of 400 cP (400 mPa-sec, #31 Spindle, 4 rpm). Red pigment (0.4 percent) was added. This printing solution was coated onto a siliconized surface of a paper substrate as described above. The resultant printed surface was laminated to a piece of STERI-DRAPE 1050 incise drape. The adhesive was peeled from the substrate, and the pattern transferred to the adhesive with coverage of 6.2 percent by area. The median distance between spots was about 0.6 mm and the median spot size was about 0.024 mm$^2$.

Example 25

A printing formulation was prepared by melting 90.75 grams of LAURICIDIN, and then adding a solution of 20 grams hydroxypropylcellulose in 297.5 grams of ethanol Then 112.5 grams of 20% CHG solution was added, and then red dye (0.1 percent) was added. The Brookfield viscosity of the solution at room temperature was 170 cP (170 mPa-sec, #21 Spindle, 6 rpm) It was coated onto a siliconized surface of a paper substrate as described above. The resultant printed surface was laminated to a piece of STERI-DRAPE 1050 incise drape. The adhesive was peeled from the substrate, and the pattern transferred to the adhesive with coverage of 4.5 percent by area. The median distance between spots was about 0.6 mm and the median spot size was about 0.016 mm$^2$.

Example 26

A 20% w/w aqueous solution of PVA (High Molecular Weight) was prepared by stirring the PVA/water mixture at elevated temperature for several days. After cooling, 150 grams of this solution was mixed with 350 grams of 20% CHG solution. 0.1% red dye was added. The Brookfield viscosity of this solution at room temperature was 230 cP (230 mPa-sec, #21 spindle, 6 rpm), and the pH was 4.7.

Phosphoric acid solution (0.05 g, 85%) was added to a 15 g portion of the above solution. The pH of this solution was measured to be 4.16. This solution was coated onto a siliconized surface of a paper substrate as described above. The resultant printed surface was laminated to a piece of STERI-DRAPE 1050 incise drape. The adhesive was peeled from the substrate, and the pattern transferred to the adhesive with coverage of 4.3 percent by area. The median distance between spots was about 0.6 mm and the median spot size was about 0.017 mm$^2$.

Example 27

Gluconic acid solution (0.45 g, approximately 50%) was added to a 15 g portion of the solution described in first paragraph of Example 26. The pH of this solution was measured to be 3.88. This solution was coated onto a siliconized surface of a paper substrate as described above. The resultant printed surface was laminated to a piece of STERI-DRAPE 1050 incise drape. The adhesive was peeled from the substrate, and the pattern transferred to the adhesive with coverage of 4.8 percent by area. The median distance between spots was about 0.6 mm and the median spot size was about 0.019 mm².

Example 28

A printing formulation was prepared by mixing 12.50 g of 20% CHG in water, 37.46 g of water, and 0.24 g of SOFTCAT SK-MH polymer on a stir plate. The sample was then put on a jar roller for two days before viscosity was measured using a Brookfield DV-I+ viscometer using the small sample adaptor set sc4-31, 280 cP, (280 millipascal-seconds). A portion of this solution was then mixed with an equal amount of ethanol and 0.05% (wt/wt) of red dye was added. It was coated onto a siliconized surface of a paper substrate as described above. The resultant printed surface was laminated to a piece of STERI-DRAPE 1050 incise drape. The adhesive was peeled from the substrate, and the pattern transferred to the adhesive with coverage of 0.5 percent by area. The median distance between spots was about 0.6 mm and the median spot size was about 0.002 mm².

Example 29

A printing formulation was prepared by mixing 12.50 g of COSMOSIL CQ PHMB in water, 37.57 g of water, and 0.24 g of SOFTCAT SK-MH polymer on a stir plate. The sample was then put on a jar roller for two days before viscosity was measured using a Brookfield DV-I+ viscometer using the small sample adaptor set sc4-31 (350 cP). A portion of this solution was then mixed with an equal amount of ethanol and 0.05% (wt/wt) of red dye was added. It was coated onto a siliconized surface of a paper substrate as described above. The resultant printed surface was laminated to a piece of STERI-DRAPE 1050 incise drape. The adhesive was peeled from the substrate, and the pattern transferred to the adhesive with coverage of 0.7 percent by area. The median distance between spots was about 0.6 mm and the median spot size was about 0.003 mm².

Example 30

A printing formulation was prepared by prepared by mixing 0.50 g of CAPMUL PG-8 propylene glycol mono-caprylate (Abitec Corp. Columbus, Ohio), 1.50 g TWEEN 20 (MP Biomedicals), 0.25 g 2-phenoxyethanol (Aldrich Chemical Co., Milwaukee, Wis.), 0.20 g ARISTOFLEX HMB, in 47.55 g of water on a stir plate. The sample was then put on a jar roller for two days before viscosity was measured using a Brookfield DV-I+ viscometer using the small sample adaptor set sc4-31, 420 cP (420 mPa-sec). A portion of this solution was then mixed with 0.1% (wt/wt) of red dye. It was coated onto a siliconized surface of a paper substrate as described above. The resultant printed surface was laminated to a piece of STERI-DRAPE 1050 incise drape. The adhesive was peeled from the substrate, and the pattern transferred to the adhesive with coverage of 0.9 percent by area. The median distance between spots was about 0.6 mm and the median spot size was about 0.003 mm².

Antimicrobial Activity Testing (Examples 28-30)

The antimicrobial activity of Examples 28-30 was measured using a direct time kill method (ASTM 2315-03 (reapproved 2008)) which is described below. A 90-minute time kill study was performed as follows.

A suspension of *Staphylococcus aureus* (ATCC #25923) was prepared at a concentration of approximately $1 \times 10^8$ CFU (colony forming units) per milliliter (mL) in phosphate buffered water (PBW) using a 0.5 McFarland Equivalence Turbidity Standard. Using an Eppendorf repeater pipettor, 50 µL of this suspension was transferred as 16 separate droplets to the adhesive surface of a 25 mm diameter section of the adhesive film. The average inoculum was 6.11 logs of bacteria. These inoculated specimens were then incubated in covered petri dishes at 35° C. (+/−2° C.) for 90 minutes. After incubation, the specimens were placed in 20 mL of Dey/Engley Neutralizing Broth (DE) and sonicated for one minute followed by vortexing for two minutes. The resulting solutions were serially diluted in PBW. The neat solution and dilutions were each plated in Trypticase Soy Agar (TSA) and incubated for 40 hours. Examples 28 and 29 each showed a microbial reduction of 99.99%. Example 30 showed a 78.75% reduction. Minimal log reduction was found for a control (STERI-DRAPE 2) specimen utilizing an otherwise comparable non-patterned substrate.

TABLE 4

|  | Example 28 | Example 29 | Example 30 | Control |
|---|---|---|---|---|
| Microbial Reduction % | 99.99 | 99.99 | 78.75 | 8.59 |
| Microbial Reduction (Log10) | 4.26 | 3.83 | 0.68 | 0.04 |

Examples 31A and 31B

A printing formulation was prepared by mixing 500 grams of a 20% w/w solution of PVA (High Molecular Weight) with 366 grams of 20% CHG solution and 354 grams of water and then adding 0.4% of red pigment. It was coated onto an acrylic release substrate as described above. The resulting pattern had an area coverage of 6.4 percent. The median distance between spots was about 0.6 mm and the median spot size was about 0.024 mm².

One sheet of this printed release substrate was coated with 50 micron thick isooctyl acrylate/N-vinylpyrrolidone (IOA/NVP, 91/9) adhesive (Example 31A) and another sheet was coated with 50 micron thick isooctyl acrylate/acrylamide IOA/ACM (97/3) adhesive (Example 31B). These adhesive coated sheets were laminated with 2SAB polyester film.

Comparative Examples A1 and A2

A sheet of an acrylic release substrate with no printing was coated with 50 micron thick isooctyl acrylate/N-vinylpyrrolidone (IOA/NVP, 91/9) adhesive (Comparative Example A1), and another sheet of the acrylic release substrate with no print was coated with 50 micron thick isooctyl acrylate/acrylamide IOA/ACM (97/3) adhesive (Comparative Example A2). These adhesive coated sheets were laminated with 2SAB polyester film.

Examples 32A and 32B

The printing formulation described in Example 31 was patterned onto a 1720 siliconized film substrate as described above. The resulting pattern had an area coverage of 3.6 percent. The median distance between spots was about 0.6 mm and the median spot size was about 0.013 mm². One sheet of this printed release substrate was coated with 50 micron thick isooctyl acrylate/N-vinylpyrrolidone (IOA/NVP, 91/9) adhesive (Example 32A) and another sheet was coated with 50 micron thick isooctyl acrylate/acrylamide IOA/ACM (97/3) adhesive (Example 32B). These adhesive coated sheets were laminated with 2SAB polyester film.

Comparative Examples B1 and B2

A sheet of 1720 siliconized film substrate with no printing was coated with 50 micron thick isooctyl acrylate/N-vinylpyrrolidone (IOA/NVP, 91/9) adhesive (Comparative Example B1), and another sheet of the 1720 siliconized film substrate with no print was coated with 50 micron thick isooctyl acrylate/acrylamide IOA/ACM (97/3) adhesive (Comparative Example B2). These adhesive coated sheets were laminated with 2SAB polyester film.

Example 33A and 33B

The printing formulation from Example 31A was patterned onto a 1752 siliconized film substrate as described above. The resulting pattern had an area coverage of 4.8 percent. The median distance between spots was about 0.6 mm, and the median spot size was about 0.19 mm². One sheet of this printed release substrate was coated with 50 micron thick isooctyl acrylate/N-vinylpyrrolidone (IOA/NVP, 91/9) adhesive (Example 33A) and another sheet was coated with 50 micron thick isooctyl acrylate/acrylamide IOA/ACM (97/3) adhesive (Example 33B). These adhesive coated sheets were laminated with 2SAB polyester film.

Comparative Examples C1 and C2

An sheet of 1752 siliconized film substrate with no printing was coated with 50 micron thick isooctyl acrylate/N-vinylpyrrolidone (IOA/NVP, 91/9) adhesive (Comparative Example C1), and another sheet of the 1752 siliconized film substrate with no print was coated with 50 micron thick isooctyl acrylate/acrylamide IOA/ACM (97/3) adhesive (Comparative Example C2). These adhesive coated sheets were laminated with 2SAB polyester film.

Release Testing for CHG Incise Drape Formulations

Specimens of the printed release substrates from Example 31, 32, and 33 were coated using a knife coater with an isooctyl acrylate/N-vinylpyrrolidone (IOA/NVP, 91/9) adhesive or isooctyl acrylate/acrylamide IOA/ACM (97/3) adhesive. A coating thickness of 50 micron was targeted. The adhesive-coated specimens were then dried in an oven at 80° C. for 5 minutes. The resultant samples were allowed to cool, and then laminated with a prime side of 2 mil polyester film 3SAB. Lamination was performed by passing the substrate bearing adhesive and the backing together through non-heated rollers, with the adhesive side facing the prime side of 2SAB film.

These specimens were then assessed for the release of printed active composition and adhesive from the release surface of the substrate. The resulting specimens were heat aged for a period of time at a constant temperature as specified in Table 5. After the desired period of aging samples were cut into a test strip of 1.27 cm wide and approximately 15 cm long. The test strips were attached to the working platen of a slip/peel tester (Model SP2000, obtained from Instrumentors, Inc., Strongsville, Ohio) using a 2.54 cm wide double-coated adhesive paper tape (commercially available from 3M company, St. Paul, Minn. under the trade designation 3M DOUBLE COATED PAPER TAPE 410B) applied to the release liner side of the test specimen. The attached test strip was rolled once on the working platen with a 2 kg rubber roller. The adhesive with polyester backing (also referred as adhesive tape) was then removed from the surface of the substrate by peeling at an angle of 180 degrees at a rate of 2.3 meters per minute (90 inches per minute), and the force required for removing the adhesive from the release liner was measured over a five-second data collection time. All release tests were carried out in a facility at constant temperature (23° C.) and constant relative humidity (50 percent). At least two measurements were made for each example, and the data are reported as an average of all measurements. Measurements were made in grams-force/0.5" and converted to gram-force/inch.

Test Method for Measuring Subsequent Adhesion

After peeling of the adhesive with polyester backing (also referred as adhesive tape) from the printed surfaces, the subsequent (180 degree peel) adhesion of the adhesive tape was measured by adhering the freshly peeled adhesive tape (without the release substrate) to a float glass test panel, with the adhesive-bearing side of the tape in contact with the panel. The adhered adhesive tape was rubbed down on the test panel, first using light thumb pressure and then with a 2 kg roller. The subsequent adhesion value of the tape was then measured using the above-described instrument and test parameters. These measurements were taken to determine whether a drop in adhesion value occurred due to the printing of CHG formulations. The subsequent adhesion test was also carried out at 23° C. and 50 percent relative humidity. At least two measurements were made for each example, and the data are reported as an average of all measurements. Measurements were made in ounces-force/0.5 inch and converted to ounces-force/inch. Results are reported in Table 5 (below).

TABLE 5

| EXAMPLE | RELEASE SUBSTRATE | ADHESIVE | AGING TIME at 60° C. | RELEASE FORCE, grams/inch | SUBSEQUENT ADHESION, ounces/inch (kg/in) |
|---|---|---|---|---|---|
| 31A | printed acrylic | IOA/NVP | 7 days | 343.8 | 46.9 (1.33) |
| 31B | printed acrylic | IOA/ACM | 7 days | 252.8 | 44.3 (1.26) |
| COMP. EX. A1 | acrylic | IOA/NVP | 7 days | 321.0 | 68.6 (1.94) |
| COMP. EX. A2 | acrylic | IOA/ACM | 7 days | 180.8 | 59.0 (1.67) |
| 32A | printed 1720 siliconized film | IOA/NVP | 7 days | 6.4 | 69.2 (1.96) |

TABLE 5-continued

| EXAMPLE | RELEASE SUBSTRATE | ADHESIVE | AGING TIME at 60° C. | RELEASE FORCE, grams/inch | SUBSEQUENT ADHESION, ounces/inch (kg/in) |
|---|---|---|---|---|---|
| 32B | printed 1720 siliconized film | IOA/ACM | 7 days | 7.1 | 26.8 (0.76) |
| COMP. EX. B1 | 1720 siliconized film | IOA/NVP | 7 days | 4.3 | 70.1 (1.99) |
| COMP. EX. B2 | 1720 siliconized film | IOA/ACM | 7 days | 3.2 | 49.5 (1.40) |
| 33A | printed 1752 siliconized film | IOA/NVP | 7 days | 25.9 | 66.0 (1.88) |
| 33B | printed 1752 siliconized film | IOA/ACM | 7 days | 23.6 | 36.5 (1.03) |
| COMP. EX. C1 | 1752 siliconized film | IOA/NVP | 7 days | 10.1 | 68.7 (1.95) |
| COMP. EX. C2 | 1752 siliconized film | IOA/ACM | 7 days | 7.0 | 52.7 (1.49) |

Examples 34-38

Examples 34-38 demonstrate the use of substrates with textured surfaces as an alternative to patterned printing.

Solutions containing polymer, CHG, and red dye were evaluated for viscosity and ability to coat a polyethylene terephthalate structured substrate (embossed or microreplicated). Several solutions were made and the viscosity measured using a Brookfield Viscometer. The solution viscosity ranged from 700 to 5000 cP (700 to 5000 mPa-sec). The samples were then coated onto the substrate using a polycarbonate doctor blade to remove the excess. The samples were placed into a 150° F. (65.5° C.) oven and allowed to dry for 10 minutes. The samples were allowed to cool, and then laminated to TEGADERM 1624W transparent dressing for further testing. Microscopy results showed that the solution had retracted and formed polymer/CHG disks in the recessed areas. The best coating was achieved when using a viscosity of 2600 cP (2.6 Pa-sec).

Example 34

A coating solution containing CHG (6%), polyvinyl alcohol (12.6%, high Mw) and red dye (0.1%) in water was prepared. It had a viscosity of 5000 cP (5000 mPa-sec). It was coated onto Structured Substrate 1. The structured pattern was laminated to a TEGADERM 1624W transparent dressing (3M Company, part number 8333-1626-05). When the adhesive was peeled from the substrate, the pattern transferred to the adhesive with an area coverage of 7.7%.

Example 35

A coating solution containing CHG (6%), polyvinyl alcohol (11.2%, high Mw) and red dye (0.1%) in water was prepared. It had a viscosity of 2600 cP (2600 mPa-sec). It was coated onto Structured Substrate 1. The structured pattern was laminated to a TEGADERM 1624W transparent dressing. When the adhesive was peeled from the substrate, the pattern transferred to the adhesive with an area coverage of 6.2%.

Example 36

The coating solution comprised CHG (6%), guar (1.9%, high Mw) and red dye (0.1%) in water, It had a viscosity of 700 cP (700 mPa-sec). It was coated onto structured substrate 1. The structured pattern was laminated to a TEGADERM 1624W transparent dressing. substrate 1. When the adhesive was peeled from the substrate, the pattern transferred to the adhesive with an area coverage of 7.0%.

Example 37

The coating solution comprised CHG (4.5%), hydroxypropylcellulose (4%), Monolaurin (14.8%), and red dye (0.1%) in ethanol/water. It had a viscosity of 170 cP (5000 mPa-sec). It was coated onto substrate 2. The structured pattern was laminated to a TEGADERM 1624W transparent dressing. When the adhesive was peeled from the substrate, the pattern transferred to the adhesive with an area coverage of 8.9%.

Example 38

A coating solution containing CHG (2%), polyvinyl pyrrolidone (1.25%), hydroxypropyl guar (1.5%, Rhodia S.A., Paris, France), and poly-glycerol-3 (55%, CAS #56090-54-1, Solvay Interox, Rheinberg, Germany) in water was prepared. The solution was allowed to stand overnight. Before use, a 10 g aliquot was thinned with 50 ml deionized water and 3 grams of isopropanol, and then coated onto structured substrate 1. After 15-30 minutes the structured pattern was laminated to the adhesive face of a piece of TEGADERM 1624W transparent dressing. When the adhesive was peeled from the substrate, the pattern transferred to the adhesive with an area coverage of 40-50%.

Examples 39 and 40

Examples 39 and 40 illustrate the use of a silicone adhesive. A silicone adhesive was prepared by combining 100 parts of OHX-4070 (Dow Corning, Midland, Mich.) with 60 parts of Wacker-Belsil TMS 803 co-hydrolysis product of tetraalkoxysilane and trimethylethoxysilane (Wacker Chemie, Munich, Germany) on a mixing roller apparatus until a clear solution was obtained. This solution was then coated onto a 2 CL PET 5100/5100 fluorosilicone-coated polyethylene terephthalate release substrate (Loparex, Willowbrook, Ill.) using a knife coater set to a 4-mil (100-micron) gap. The coated specimen was then e-beam cured with 6 Mrads at 300 keV. The cured specimen was then laminated to ESTANE 58237 polyurethane film (available from Lubrizol Corp., Wickliffe, Ohio) as follows. The substrate was removed and the adhesive specimen with film was laminated by hand rolling onto the printed pattern from Examples 1 and 6, resulting in Examples 39 and 40, respectively.

The substrate was then removed from the adhesive. The CHG pattern was observed to have transferred to the adhesive. The samples also showed antimicrobial activity when used for Zone of Inhibition experiments.

Example 41

A printing formulation was prepared by mixing 150 grams of a 20% w/w solution of PVA (High Molecular Weight) with 350 grams of 20% CHG solution, and then adding 0.1% of red dye. It had a Brookfield Viscosity of 230 cP (Room Temperature, 6 rpm, Spindle S21) and a pH of 4.7. It was coated onto a SILFLU M117 film (fluorosilicone-coated polyester film from Siliconature, USA, LLC, Chicago, Ill.) using the method of Example 18. The resultant printed surface was laminated to a piece of STERI-DRAPE 1050 incise drape. The adhesive was peeled from the substrate, and the pattern transferred to the adhesive with coverage of 3.4 percent by area. The median distance between spots was about 0.6 mm and the median spot size was about 0.012 $mm^2$.

Example 42

The printing formulation from Example 41 was coated onto an SBOPP 9741 release liner (3M SCOTCHPAK 9741 RELEASE LINER from 3M, St. Paul, Minn. 55144) using the method described in Example 18. The resultant printed surface was laminated to a piece of STERI-DRAPE 1050 incise drape. The adhesive was peeled from the substrate, and the pattern transferred to the adhesive with coverage of 7.0 percent by area. The median distance between spots was about 0.6 mm and the median spot size was about 0.025 $mm^2$.

Example 43

The printing formulation from Example 41 was coated onto a low adhesion backsize treated surface of a film prepared by coating a silicone acrylate, using the method described in Example 18. A 0.02 mm thick isooctyl acrylate/ N-vinylpyrrolidone (IOA/NVP, 91/9) adhesive prepared generally according to the disclosure in U.S. Pat. No. 5,032,460 (Kantner et al.) was coated over the printed pattern. The film was then rolled onto itself such that the adhesive surface contacted the non-backsize-treated surface of the film. After 24 hours, the sample was unrolled, and the adhesive had been transferred to the non-backsized surface of the film. The printed pattern was then exposed on the surface of the adhesive with coverage of 7.4% percent by area. The median distance between spots was about 0.6 mm and the median spot size was about 0.030 $mm^2$.

SELECT EMBODIMENTS OF THE PRESENT DISCLOSURE

In a first embodiment, the present disclosure provides a method of making a pressure-sensitive adhesive article, the method comprising:

contact printing an active composition onto a surface of a substrate to form a printed surface, whereby the active composition spontaneously dewets the surface of the substrate to form active deposits on the surface of the substrate, wherein the active composition comprises an active agent dissolved or dispersed in an aqueous liquid vehicle; and disposing a pressure-sensitive adhesive layer on the printed surface.

In a second embodiment, the present disclosure provides a method according to the first embodiment, wherein, as initially contacted with the surface of the substrate, the active composition contacts a first area of the surface of the substrate, and wherein the active deposits contact a second area of the surface of the substrate, and wherein the second area is less than or equal to 50 percent of the first area.

In a third embodiment, the present disclosure provides a method according to the first or second embodiment, wherein the active composition further comprises a hydratable polymer.

In a fourth embodiment, the present disclosure provides a method according to any one of the first to third embodiments, wherein the active agent comprises at least one non-volatile component.

In a fifth embodiment, the present disclosure provides a method according to the any one of the first to fourth embodiments, wherein the active agent comprises at least one of an antimicrobial agent, a topical antiseptic, or a cationic antiseptic.

In a sixth embodiment, the present disclosure provides a method according to any one of the first to fifth embodiments, wherein the active agent comprises chlorhexidine gluconate.

In a seventh embodiment, the present disclosure provides a method according to the fifth or sixth embodiment, wherein the active agent comprises a polymer.

In an eighth embodiment, the present disclosure provides a method according to any one of the first to seventh embodiments, wherein the surface of the substrate comprises at least one of a silicone polymer, fluoropolymer, or acrylic polymer.

In a ninth embodiment, the present disclosure provides a method according to any one of the first to eighth embodiments, wherein the surface of the substrate is microstructured.

In a tenth embodiment, the present disclosure provides a method according to any one of the first to ninth embodiments, wherein the active deposits are arranged in an array on the surface of the substrate.

In an eleventh embodiment, the present disclosure provides a method according to any one of the first to tenth embodiments, wherein the contact printing comprises flexographic printing.

In a twelfth embodiment, the present disclosure provides a method according to any one of the first to eleventh embodiments, wherein the contact printing comprises roll coating.

In a thirteenth embodiment, the present disclosure provides a method according to any one of the first to twelfth embodiments, wherein the contact printing comprises knife coating or doctor blade coating.

In a fourteenth embodiment, the present disclosure provides a method according to any one of the first to thirteenth embodiments, further comprising removing at least a portion of the liquid vehicle from the active composition after it is contact printed onto the surface of the substrate, but before the pressure-sensitive adhesive layer is disposed on the printed surface.

In a fifteenth embodiment, the present disclosure provides a method according to any one of the first to fourteenth embodiments, wherein, prior to contacting the surface of the substrate, the pressure-sensitive adhesive is disposed on a backing.

In a sixteenth embodiment, the present disclosure provides a method according to any one of the first to fifteenth embodiments, wherein the pressure-sensitive layer is formed by coating a pressure-sensitive adhesive composition on the printed surface.

In a seventeenth embodiment, the present disclosure provides a method according to any one of the first to sixteenth embodiments, wherein at least a portion of the backing is transparent or translucent.

In an eighteenth embodiment, the present disclosure provides a method according to any one of the first to seventeenth embodiments, wherein at least a portion of the backing and at least a portion of the pressure-sensitive adhesive layer are transparent or translucent.

All patents and publications referred to herein are hereby incorporated by reference in their entirety. Various modifications and alterations of this disclosure may be made by those skilled in the art without departing from the scope and spirit of this disclosure, and it should be understood that this disclosure is not to be unduly limited to the illustrative embodiments set forth herein.

What is claimed is:

1. A method of making a pressure-sensitive adhesive article, the method comprising:
    contact printing an active composition onto a surface of a release substrate to form a printed surface, whereby the active composition spontaneously dewets the surface of the release substrate to form active deposits on the surface of the release substrate, wherein the active composition comprises an active agent dissolved or dispersed in an aqueous liquid vehicle; and
    disposing a pressure-sensitive adhesive layer on the printed surface.

2. The method of claim 1, wherein, as initially contacted with the surface of the release substrate, the active composition contacts a first area of the surface of the release substrate, and wherein the active deposits contact a second area of the surface of the release substrate, and wherein the second area is less than or equal to 50 percent of the first area.

3. The method of claim 1, wherein the active composition further comprises a hydratable polymer.

4. The method of claim 1, wherein the active agent comprises at least one non-volatile component.

5. The method of claim 1, wherein the active agent comprises at least one of an antimicrobial agent, a topical antiseptic, or a cationic antiseptic.

6. The method of claim 1, wherein the active agent comprises chlorhexidine gluconate.

7. The method of claim 1, wherein the active agent comprises a polymer.

8. The method of claim 1, wherein the surface of the release substrate comprises at least one of a silicone polymer, fluoropolymer, or acrylic polymer.

9. The method of claim 1, wherein the surface of the release substrate is microstructured.

10. The method of claim 1, wherein the active deposits are arranged in an array on the surface of the release substrate.

11. The method of claim 1, wherein the contact printing comprises flexographic printing.

12. The method of claim 1, wherein the contact printing comprises gravure roll coating.

13. The method of claim 1, wherein the contact printing comprises knife coating or doctor blade coating.

14. The method of claim 1, further comprising removing at least a portion of the liquid vehicle from the active composition after it is contact printed onto the surface of the release substrate, but before the pressure-sensitive adhesive layer is disposed on the printed surface.

15. The method of claim 1, wherein, prior to contacting the surface of the release substrate, the pressure-sensitive adhesive is disposed on a backing.

16. The method of claim 15, wherein at least a portion of the backing is transparent or translucent.

17. The method of claim 15, wherein at least a portion of the backing and at least a portion of the pressure-sensitive adhesive layer are transparent or translucent.

18. The method of claim 1, wherein the pressure-sensitive layer is formed by coating a pressure-sensitive adhesive composition on the printed surface.

* * * * *